US010201633B2

(12) United States Patent
Weinberger et al.

(10) Patent No.: US 10,201,633 B2
(45) Date of Patent: Feb. 12, 2019

(54) GLASS COMPOSITES FOR TISSUE AUGMENTATION, BIOMEDICAL AND COSMETIC APPLICATIONS

(71) Applicants: Augusta University Research Institute, Inc., Augusta, GA (US); Applied Research Center, Inc., Aiken, SC (US)

(72) Inventors: Paul M. Weinberger, Augusta, GA (US); William D. Hill, Augusta, GA (US); George G. Wicks, Aiken, SC (US)

(73) Assignees: Augusta University Research Institute, Inc., Augusta, GA (US); Applied Research Center, Inc., Aiken, SC (US)

( * ) Notice: Subject to any disclaimer, the term of this patent is extended or adjusted under 35 U.S.C. 154(b) by 0 days.

(21) Appl. No.: 15/532,645

(22) PCT Filed: Dec. 7, 2015

(86) PCT No.: PCT/US2015/064252

§ 371 (c)(1),
(2) Date: Jun. 2, 2017

(87) PCT Pub. No.: WO2016/090359

PCT Pub. Date: Jun. 9, 2016

(65) Prior Publication Data

US 2017/0354755 A1 Dec. 14, 2017

Related U.S. Application Data

(60) Provisional application No. 62/088,027, filed on Dec. 5, 2014.

(51) Int. Cl.

| | |
|---|---|
| ***A61L 27/10*** | (2006.01) |
| ***A61K 9/50*** | (2006.01) |
| ***A61Q 19/08*** | (2006.01) |
| ***A61K 8/02*** | (2006.01) |
| ***C09C 1/28*** | (2006.01) |
| ***A61L 27/26*** | (2006.01) |
| ***A61L 27/54*** | (2006.01) |
| ***A61L 27/20*** | (2006.01) |
| ***A61L 27/24*** | (2006.01) |
| ***A61L 27/34*** | (2006.01) |
| ***A61L 27/52*** | (2006.01) |
| ***A61L 27/56*** | (2006.01) |
| ***C03C 4/00*** | (2006.01) |
| ***C03C 11/00*** | (2006.01) |

(52) U.S. Cl.

CPC ............ *A61L 27/10* (2013.01); *A61K 8/0279* (2013.01); *A61K 9/50* (2013.01); *A61K 9/5005* (2013.01); *A61L 27/20* (2013.01); *A61L 27/24* (2013.01); *A61L 27/26* (2013.01); *A61L 27/34* (2013.01); *A61L 27/52* (2013.01); *A61L 27/54* (2013.01); *A61L 27/56* (2013.01); *A61Q 19/08* (2013.01); *C03C 4/0007* (2013.01); *C03C 11/002* (2013.01); *C09C 1/28* (2013.01); *A61K 2800/412* (2013.01); *A61K 2800/651* (2013.01); *A61K 2800/91* (2013.01); *A61L 2400/06* (2013.01); *A61L 2430/02* (2013.01); *A61L 2430/22* (2013.01); *A61L 2430/30* (2013.01); *A61L 2430/34* (2013.01); *C01P 2004/32* (2013.01); *C01P 2004/34* (2013.01); *C01P 2004/61* (2013.01); *C01P 2006/22* (2013.01); *C03C 2204/00* (2013.01)

(58) Field of Classification Search

None

See application file for complete search history.

(56) References Cited

U.S. PATENT DOCUMENTS

| | | | | |
|---|---|---|---|---|
| 5,849,331 | A | 12/1998 | Ducheyne et al. | |
| 6,197,342 | B1 | 3/2001 | Thut et al. | |
| 6,413,538 | B1 | 7/2002 | Garcia et al. | |
| 6,869,445 | B1 | 3/2005 | Johnson | |
| 7,131,997 | B2 * | 11/2006 | Bourne | A61F 2/0036 623/23.72 |
| 8,535,725 | B2 | 9/2013 | Li et al. | |
| 2002/0151466 | A1 | 10/2002 | Hubbard et al. | |
| 2004/0091543 | A1 * | 5/2004 | Bell | A61B 17/12022 424/489 |
| 2007/0128244 | A1 | 6/2007 | Smyth | |
| 2008/0035020 | A1 | 2/2008 | Schnorrer | |
| 2008/0038305 | A1 | 2/2008 | Kotze et al. | |
| 2010/0129455 | A1 | 5/2010 | Murase et al. | |
| 2010/0139320 | A1 * | 6/2010 | Schumacher | C01B 3/0084 65/21.4 |

(Continued)

FOREIGN PATENT DOCUMENTS

| | | |
|---|---|---|
| DE | 10 2004 021700 | 11/2005 |
| EP | 0 251 695 | 1/1988 |

(Continued)

OTHER PUBLICATIONS

Brook, I.M, et al., "Glass-Ionomers: Bioactive Implant Materials", Biomaterials 19 (6): pp. 565-571 Mar. 1998.

(Continued)

*Primary Examiner* — Susan T Tran
(74) *Attorney, Agent, or Firm* — Smith Gambrell & Russell LLP

(57) ABSTRACT

Compositions and methods for glass composites suitable for tissue augmentation, biomedical, and cosmetic applications are provided. The glass microsphere component of the composites are biologically inert, non-reactive and act as a nearly permanent tissue filler. One embodiment provides a tissue augmentation composite containing an effective amount of solid glass microspheres, hollow glass microspheres, porous wall hollow glass microspheres, or combinations thereof with a suitable biocompatible matrix to serve as a bulking agent when injected into a patient. The compositions can be used for soft or hard tissue augmentation as well as delivery of cargos on demand.

16 Claims, 10 Drawing Sheets

(56) References Cited

U.S. PATENT DOCUMENTS

| | | | | |
|---|---|---|---|---|
| 2011/0038938 | A1 | 2/2011 | Ison et al. | |
| 2011/0229576 | A1* | 9/2011 | Trogler | A61K 9/0019 424/490 |
| 2012/0164187 | A1 | 6/2012 | Olula et al. | |
| 2012/0265167 | A1 | 10/2012 | Simonson et al. | |
| 2012/0276164 | A1 | 11/2012 | Tuominen et al. | |
| 2013/0157956 | A1 | 6/2013 | Kluijtmans et al. | |

FOREIGN PATENT DOCUMENTS

| | | |
|---|---|---|
| WO | 9404657 | 3/1994 |
| WO | WO 00/30561 | 6/2000 |
| WO | 200629621 | 3/2006 |
| WO | WO 2011/008939 | 1/2011 |

OTHER PUBLICATIONS

Cordioli, Giampiero, et al., "Maxillary Sinus Floor Augmentation Using Bioactive Glass Granules and Autogenous Bone with Simultaneous Implant Placement: Clinical and Histological Findings", Clin Oral Implants Res 12 (3): pp. 270-276 (Jan. 2001).

Fischer, Joerg, M.D., et al., "Cosmetic Permanent Fillers for Soft Tissue Augmentation: a New Contraindication for Interferon Therapies", Archives of Dermatology 143, No. 4, pp. 507-510 (2007).

Johnson, A., et el., "Osteoconductivity of Modified Fluorcanasite Glass-Ceramics for Bone Tissue Augmentation and Repair", Journal of Biomedical Materials Research Part A 94, No. 3, pp. 760-768. (2010).

Lemperle, Gottfried, et al., "ArteFill® Permanent Injectable for Soft Tissue Augmentation: I. Mechanism of Action and Injection Techniques", Aesthetic Plastic Surgery vol. 34, Issue 3, pp. 264-272 (Jun. 2010).

Li, S., et al., "Porous-wall Hollow Glass Microspheres as Novel Potential Nanocarriers . . . ", Nanomedicine: Nanotechnology, Biology and Medicine, vol. 6, No. 1, 128-134 (2010).

International Search Report and Written Opinion issued by the European Patent Office dated Jul. 8, 2016; 18 pages.

Communication Pursuant to Article 94(3) EPC issued by the European Patent Office dated Sep. 21, 2018 for corresponding European Application No. 15 825 672.7; 4 pages.

* cited by examiner

GLASS COMPOSITES FOR TISSUE AUGMENTATION, BIOMEDICAL AND COSMETIC APPLICATIONS

CROSS-REFERENCE TO RELATED APPLICATIONS

This application claims benefit of and priority to U.S. Provisional patent application 62/088,027 filed on Dec. 5, 2014, and is incorporated in its entirety where permissible.

FIELD OF THE INVENTION

The invention is generally directed to implants, kits and methods of use thereof. More specifically, the implants are composites consisting of glass microspheres and biocompatible matrices.

BACKGROUND OF THE INVENTION

Soft tissue augmentation with injectable fillers is widely used for cosmetic improvements and a variety of medical applications. In cosmetic procedures, fillers are used primarily to improve aesthetic appearance including scar revision, reduction in wrinkles, restoration of lost skin volume, and elimination of concavities or depressions. Other cosmetic procedures involve injection or implant of colorants, dyes, or inks to produce externally visible pigmentation or coloration. In medical applications, biomedical fillers are used to augment soft tissue volume in the larynx (to improve phonation, and/or to reduce aspiration from incomplete glottic closure). They are used in other areas of the body to augment the function of natural biological valves, such as the upper or lower esophageal sphincter, the anal sphincter, and urethral sphincters. Other medical applications of biomedical fillers include bridging or reinforcement of bone defects or fractures, particularly in the case of non-union.

Fillers known to those skilled in the art to be used for cosmetic and medical improvements include hyaluronic acid, calcium hydroxylapatite, and poly-L-lactic acid (Vleggaar et al., *Journal of drugs in dermatology,* 13(4 Suppl): s40-43 (2014)). While widely used, these dermal fillers are not permanent and need reapplication at 6-9 months for hyaluronic acid, 10-14 months for calcium hydroxylapatite (Emer and Sundaram, *Journal of Drugs in Dermatology,* 12(12):1345-54 (2013), and about every 24 months for poly L-lactic acid fillers (Vleggaar et al., *Journal of drugs in dermatology,* 13(4 Suppl):s40-43 (2014); Vleggaar et al., *Journal of drugs in dermatology,* 13(4 Suppl):s44-51 (2014); and Mest and Humble, *Dermatologic Surgery,* 35(Suppl 1):350-359 (2009)).

Other fillers commonly known to those skilled in the art to improve bone defects or fractures include decellularized and processed allogenic bone pate, mineralized and processed collagen particles, synthetic tricalcium phosphate particles, and various mixtures of calcium hydroxyappetite and/or calcium sulfate (e.g. Cerament™).

For all of the above categories, many of these fillers induce an unacceptable inflammatory response making them less than ideal for cosmetic or surgical procedures (Cecchi, et al., *Dermatology,* 228(1):14-17 (2014)). Additionally, many of these substances also have high viscosity, making it difficult for them to pass through thin needles used in clinical applications.

Therefore, it is an object of the invention to provide compositions and methods of tissue augmentation, coloration, and/or cargo delivery that are long lasting, easy to administer and evoke limited inflammatory responses.

It is another object of the invention to provide biomedical composites having a controlled and reduced viscosity.

It is another object of the invention to provide prepackaged, ready-to-use composites for tissue augmentation, biomedical, or cosmetic applications.

SUMMARY OF THE INVENTION

Compositions and methods for a composite useful for the purposes of tissue augmentation, biomedical, or cosmetic applications are provided. In one embodiment the composites are biologically inert, non-reactive and act as near permanent tissue filler designed to endure in place. Another embodiment provides a tissue augmentation composite containing an effective amount of solid glass microspheres, hollow glass microspheres, porous wall hollow glass microspheres, or combinations thereof to serve as a bulking agent when injected into a patient. The composites are useful for soft or hard tissue augmentation, cosmetic procedures, and other biomedical applications.

The glass microspheres can also be coated for improved properties. In certain embodiments, the microspheres are coated with a synthetic polymer, a naturally occurring polymer, or combinations thereof. The coating agent can be blends of polymers or other materials. The coating agent can be selected according to the function the coating agent provides to the microspheres. For example, the microspheres can be coated with an agent that reduces, inhibits, or prevents an immunological reaction to the microspheres when the microspheres are administered to a subject, for example a human subject. Other coatings can be used to improve mechanical and/or chemical properties of the microspheres. Other coatings can also be selected that slow or delay the release of an active substance if loaded into the microspheres. Exemplary active agents include but are not limited to growth factors, chemotactic substances, chemokines, cytokines, ribonucleic acid (RNA), deoxyriboneucleic acid (DNA), steroids, chemotherapy agents, osteogenic agents, antibiotics, and antibodies.

Methods for using the disclosed glass microsphere compositions in soft and hard tissue augmentation as well as delivery of cargos or payloads are also provided.

Kits containing a composite including glass microspheres of various combinations, and an aqueous matrix of tailored viscosity in preloaded syringes are also described.

BRIEF DESCRIPTION OF THE DRAWINGS

The accompanying drawings, which are incorporated in and constitute a part of this specification, illustrate several aspects described below.

FIG. 1A shows typical distributions of glass microsphere sizes and types. FIG. 1B is a cross section of a glass microsphere demonstrating the interconnected wall porosity typical of a porous wall hollow glass microsphere.

DETAILED DESCRIPTION OF THE INVENTION

I. Definitions

Figures 1A, 1B:
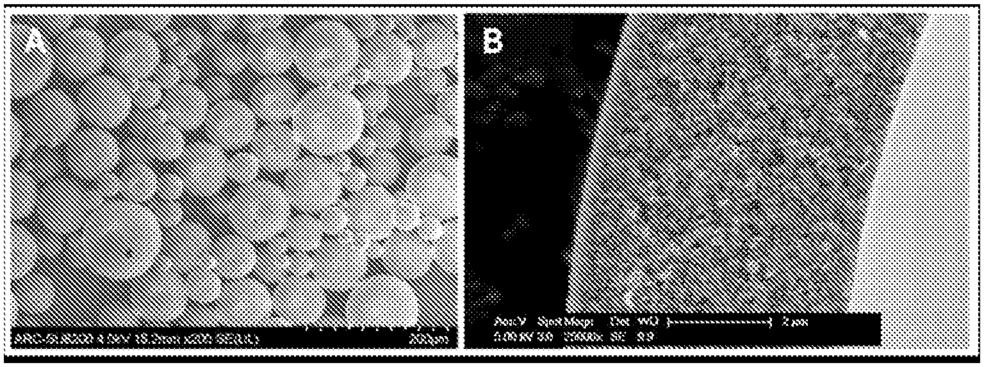
FIGS. 1A and 1B are microphotograghs.

The term "bulking agent" refers to an agent that increases the thickness or volume of a tissue when injected into the tissue.

The term "permanent" with reference to bulking agents refers to a relatively non-biodegradable, non-absorbable bulking agent, for example glass microspheres in a compatible, tailored viscosity medium.

The term "glass microspheres" refers to spheres of glass having a diameter of less than 1 mm and includes solid glass microspheres, hollow glass microspheres and/or porous wall hollow glass microspheres, all with smooth surfaces to facilitate packing and delivery, and minimize immunologic response Preferred diameters are 10 to 100 μm, a more preferable diameter 20-60 μm.

The term "composite" refers to a combination consisting of various types of glass microspheres in optimized ratios, size distributions and quantities, combined with a biocompatible fluid or gel matrix optimized for the applications desired. This combination results in unique properties of the composite compared to the properties of each of the individual components alone.

The term "biological molecule" refers to any carbohydrate, lipid, protein, ribonucleic acid, deoxyribonucleic acid, antibody or fragment thereof, proteoglycans, glycoproteins, or combination of these.

The term "soft tissue augmentation", as used herein, refers to any type of volume augmentation of soft tissues, including, but not limited to, facial contouring (e.g., more pronounced cheeks or chin), breast augmentation or reconstruction after mastectomy, correction of concave deformities (e.g., post-traumatic, HIV associated lipoatrophy) and correction of deep age-related facial folds. Thus, soft tissue augmentation may be used solely for cosmetic purposes or for medical purposes, such as following trauma or degenerative disease.

The term "soft tissue", as used herein, refers to tissues that connect, support, or surround other structures and organs of the body. Soft tissue includes muscles, fibrous tissues and fat.

The term "subject or patient" refers to a mammal, primate and preferably a human.

The terms "subepidermal administration" or "subcuticular administration", as used herein, refer to administration beneath the epidermis of the skin, including administration into the dermis, subcutis or deeper, such as submuscularly, or into the periosteum where applicable (in the vicinity of bone tissue.

The term "implant", as used herein, refers widely to any type of implanted or implantable foreign object or material. Implants also include objects or materials that are nearly identical to non-foreign objects or materials. The implant according to the invention is not limited to any particular shape. The final shape of the implant in the body is decided by the skilled practitioner for the purpose of the treatment.

The term "Flow Readily" refers to a material, designed to be implanted by injecting through a syringe and needle, that has low viscosity and/or low force required to eject the material from the syringe such that effort required is comfortable to the practitioner injecting the material.

The term "near permanent" with reference to bulking agents refers to a material with one or more components being relatively non-biodegradable, non-absorbable such that substantial degradation or destruction of the component is not likely to occur within the context of a normal human life span, for example glass microspheres in a compatible, tailored viscosity medium. Preferably the relatively non-biodegradeable component makes up a majority (>50% vol/vol) of the composite, and more preferably >75% of the composite.

II. Glass Microsphere Composites

The disclosed composites contain solid glass microspheres, hollow glass microspheres, porous wall hollow glass microspheres, or combinations thereof together with a biocompatible matrix. In some embodiments this matrix is a fluid (sol). In other embodiments this matrix is a gel, and in still other embodiments this matrix is convertible between sol and gel phases. One embodiment provides glass microspheres having a diameter of less than 1 mm and greater than 1 μm. In some embodiments, the glass microspheres have a diameter ranging from about 2 μm to about 500 μm or 2 to 300 μm or 10 to 100 μm. Preferred diameters are 10 to 50 μm, or 10 to 60 μm, and more preferred diameters are 5 to 20 μm, 20 to 40 μm, 20 to 60 μm, or 40 to 60 μm. The diameter of the glass microspheres are typically of a dimension that allows the composite to be easily implanted into a patient. In one embodiment the composite is implanted by injection. In a preferred embodiment the injection is performed through a needle with a diameter ranging from about 30 to about 18 gauge. In a more preferred embodiment the injection is performed through a 21, 23, or 25-gauge needle.

The glass microspheres can be all the same diameter or can have multiple diameters in the described ranges. In certain embodiments, the microspheres are all one type, and in other embodiments, multiple types of microspheres are combined.

In certain embodiments, the glass microspheres are coated. The glass microspheres can be coated with a chemical, element, drug, biological molecule, polymer or a combination thereof. The coating can contain or be attached to, a moiety allowing targeting of the glass microspheres to a specific organ, tissue or cell type.

Hollow glass microspheres and porous wall hollow microspheres (hereafter referred to collectively as hollow microspheres) can be loaded with cargo including but not limited to biological molecules, chemicals, elements, or other materials. In one embodiment the cargo can be a pigment or coloring agent. The hollow microspheres can be loaded with one or more therapeutic agents such as antibiotics, anti-inflammatory agents, growth factors, cytokines, chemokines, chemotherapeutic agents, cytotoxic agents, antibodies, or combinations thereof. The hollow microspheres can be loaded with cargo of living biological elements such as cells, bacteria, viruses, or combinations thereof. The cargos above can exist alone or in various combinations. The loaded glass microspheres can be modified to delay or extend the release of cargo from the glass microspheres once the glass microspheres have been administered to a subject.

The glass microsphere composites are useful as bulking agents for tissue augmentation and as a means for delivering therapeutic substances. The biocompatible matrix and various types and ratios of microspheres to matrix can be formulated using conventional techniques. Density, sizes and size distributions of microspheres, viscosities of solutions, can be modulated for desired uses.

A. Solid Glass Microspheres

1. Commercially Available Solid Glass Microspheres

Some embodiments include solid glass microspheres, alone or in combination with other microspheres. The methods for the manufacture of solid glass microspheres is well known to those skilled in the art, and solid glass microspheres are commercially available for example from a variety of sources including, but not limited to Potters Industries LLC, CoSpheric Innovations and Microtechnology, and MoSci Corp., and Polysciences, Inc. Exemplary solid glass microspheres are made of borosilicate or soda-lime. The microspheres are typically sieved to specific diameter ranges, and they are provided in powder form.

2. Methods of Making

A number of processes have been devised for the production of spherical glass bodies in small sizes. These generally involve the free suspension of particles in a hot zone for a time and at a temperature sufficient to permit each particle to be drawn into a spherical shape by surface tension. For economical commercial production of glass microspheres it is important that the viscosity of the glass generally be relatively low at a reasonable melting temperature (for example, no greater than about 1350° C.). Generally, additions of alkali and fluorine are used to reduce viscosity and melting temperature; however, the use of fluorine creates an environmental concern as it is readily lost during the melting process and the addition of alkali typically results in microspheres that are of lower chemical durability and that are hydrophobic and tend to clump and be poorly flowing (See U.S. Pat. No. 6,765,720). However, other agents can also be added to increase or improve the 'flowability' of the microspheres.

Bio-active particulate glass may be prepared according to the methods of the art such as taught in U.S. Pat. Nos. 4,159,358; 4,234,972; 4,103,002; 4,189,325; 54,171,544; 4,775,646; 4,857,046, 5,074,916 and 5,840,290. For example, the raw materials (e.g., $SiO_2$, CaO, $Na_2O$ and $P_2O_5$) are mixed in Nalgene® plastic container on a ball mill for four hours. The mix is then melted in a platinum crucible at 1350° C. and homogenized for 24 hours. The molten glass is poured into distilled, deionized water to produce a glass frit. The frit is ground in a mortar and pestle and passed through ASTM sieves to produce the required particle size range.

B. Hollow Glass Microspheres

1. Commercially Available Hollow Glass Microspheres

Several embodiments provide composites containing hollow glass microspheres. The manufacture of hollow glass microspheres is well known by those skilled in the art, and hollow glass microspheres are commercially available for example from 3M (St. Paul, Minn.), Bariteworld (Rockleigh, N.J.) and other sources.

2. Methods of Making Hollow Glass Microspheres

Hollow glass microspheres can be produced by a variety of techniques. In one approach, glass powder along with a blowing agent is fed into a hot zone in a furnace, which softens the glass to allow formation of spherical particles. The blowing agent becomes unstable as it is heated, producing a glass bubble that expands to produce hollow glass microspheres. The material is quenched, and a flotation process is used to retrieve the desired initial products.

C. Porous-Wall Hollow Glass Microspheres

Suitable porous wall hollow glass microspheres can be produced according to the methods taught in U.S. Pat. Nos. 7,666,807 and 8,535,725 both of which are incorporated by reference in their entireties. These porous wall hollow glass microspheres can be obtained from commercial sources such as MoSci Corp (Rolla, Mo.). Briefly, feed for producing porous wall hollow glass microspheres is a 20- to 40-μm sodium borosilicate glass powder, and containing a sulfate blowing agent. The powder is fed into a hot zone produced by a controlled gas-air flame, which softens the glass to allow formation of spherical particles. The blowing agent becomes unstable as it is heated, producing a glass bubble that expands to produce hollow glass microspheres. The material is quenched, and a flotation process is used to retrieve the desired initial products. The hollow glass microspheres are then converted into porous wall hollow glass microspheres by heat treating to produce two glass phases in the thin outer walls, one rich in silica and the other in sodium and boron They are then leached in hydrochloric acid, which preferentially leaches the sodium- and boron-rich phase, leaving behind interconnected channels in the silica-rich phase and through wall porosity. Dry sieving can then be performed to produce uniform and specific sizes or alternatively, produce wider size distributions as desired.

An exemplary hollow glass microsphere has a porous wall surrounding an internal volume. The porous wall can have a unique pore morphology and diameter of about 1 nanometer (nm) to about 100 nm. In some embodiments, the porous wall has a pore diameter of about 10 nanometers (nm).

The pores within the walls of the porous wall hollow glass microspheres can be gated with a gating agent. In one embodiment the gating agent is a sol-gel glass. In another embodiment, the gating agent is a dopant added to the base glass composition. In still another embodiment, the gating agent is a polymer, biological molecules, colloidal starch, polymerized fibrin, or chemical.

The outer surface of the various types of microspheres can be coated to enhance properties and uses, and are further described below. In one embodiment, the microspheres are coated with a compound, biological molecule, or polymer. In one preferred embodiment the coating is polyvinylpyrrolidone.

To emphasize, a unique feature of the Porous Wall Hollow Glass Microspheres is that a through-wall, interconnected porosity can be created and controlled through the thin outer shells, due to the glass composition and heat-treatments used, which can produce phase separation and two different glass phases in the outer shells. One of these phases is an interconnected worm-like structure of a relatively soluble composition that when leached, can produce a very unique through-wall porosity that can be controlled on a scale of about 1 to 100 nm. The porosity allows filling of the microspheres with a variety of cargos (liquids, gases or solids) for a variety of potential applications.

1. Cargo

The porous wall hollow glass microspheres can be loaded with one or more tissue augmenting, therapeutic, prophylactic or diagnostic agents, for example by immersing the porous wall hollow glass microspheres in a solution of the cargo or by forcing solution into the "protective cocoons" and precipitating solids within. For example, the microspheres are taken from dry formulation and loaded in a solution (either aliphatic or aqueous) and then sealed. Alternatively a precipitant can be induced within the spheres either by supersaturation and then induced crystal formation, or drying/evaporating the carrier. These agents can be dyes, pigments, or coloring agents, proteins, peptides, amino acids, nucleic acids, carbohydrates, lipids, small molecules, antibiotics, chemotherapeutic agents, contrast agents (such as metals, ferromagnetic agents, or carbon nanoparticles) or combinations thereof. In some embodiments different microspheres are loaded with different therapeutic agents forming a heterogenous mixture of microspheres. Exemplary therapeutic agents include, but are not limited to, antibiotics, anti-inflammatory agents, chemotherapeutic agents, analgesics, hormones, steroids, cytotoxic agents, growth factors, cytokines, and combinations thereof.

The glass microspheres can be loaded with oligonucleotides such as iRNA, RNA, DNA, and siRNA. The oligonucleotides can be single or double stranded. The oligonucleotides can be designed to inhibit or reduce the expression of targeted genes or to activate the expression of targeted genes. In one embodiment, the oligonucleotides are designed to induce expression of genes involved with tissue regeneration, wound healing, or both.

The glass microspheres can be loaded with one or more growth factors. Growth factors include, but are not limited to adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), healing factor, hepatocyte growth factor (HGF), hepatoma-derived growth factor (HDGF), insulin-like growth factor (IGF), keratinocyte growth factor (KGF), migration-stimulating factor, myostatin (GDF-8), nerve growth factor (NGF) and other neurotrophins, platelet-derived growth factor (PDGF), thrombopoietin (TPO), transforming growth factor alpha (TGF-α), transforming growth factor beta (TGF-β) types 1, 2 or 3, tumor necrosis factor-alpha (TNF-α), vascular endothelial growth factor (VEGF), Wnt and Wnt Signaling Pathway molecules, placental growth factor (PGF), [(Fetal Bovine Somatotrophin)] (FBS), IL-1-Cofactor for IL-3 and IL-6, IL-2, IL-3, IL-4, IL-5, IL-6, and IL-7.

The hollow glass microspheres can contain one or more chemokines including, but not limited to CC chemokines, CXC chemokines, C chemokines, and CXC3 chemokines. CC chemokines include: CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. CXC chemokines include: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. C chemokines include: XCL1 and XCL2. CXC3 chemokines include CX3CL1.

The porous wall hollow glass microspheres can be loaded with antimicrobial agents. Representative antimicrobial agents include antibiotics, anti-fungals, anti-protozoa, and antimicrobial metals such as silver, silver crystals, silver nanocrystals, and silver ions.

Anti-Fungal Agents

A variety of known antifungal agents can be used to prepare the described compositions. A list of potential antifungal agents can be found in "Martindale—The Complete Drug Reference", 32nd Ed., Kathleen Parfitt, (1999) on pages 367-389. Suitable antifungals include, without limitation, amphotericin, amorolfine, bifonazole, bromochlorosalicyanilide, buclosamide, butenafine, butoconazole, candicidin, chlordantoin, chlormidazole, chlorphenesin, chlorxylenol, ciclopirox olamine, cilofungin, clotrimazole, croconazole, eberconazole, econazole, enilconazole, fenticlor, fenticonazole, fluconazole, flucytosine, griseofulvin, hachimycin, haloprogin, hydroxystilbamine, isethionate, iodochlorohydroxyquinone, isoconazole, itraconazole, ketoconazole, lanoconazole, luflucarban, mepartricin, miconazole, naftifine, natamycin, neticonazole, nifuroxime, nystatin, omoconazole, oxiconazole, pentamycin, propionic acid, protiofate, pyrrolnitrin, ravuconazole, saperconazole, selenium sulfide, sertaconazole, sulbentine, sulconazole, terbinafine, terconazole, tioconazole, tolciclate, tolnaftate, triacetin, timidazole, undecenoic acid, voriconazole and combinations thereof. Some of these agents are known to have antibacterial activity as well.

In one embodiment, the anti-fungal agent(s) is an azole. Suitable imidazole and triazole antifungal agents are fluconazole, timidazole, secnidazole, miconazole nitrate, econazole, haloprogin, metronidazole, itraconazole, terconazole, posaconazole, ravuconazole, ketoconazole, clotimazole, sapirconazole and combinations thereof.

In an alternative embodiment, the anti-fungal agent(s) is chlorxylenol, undecyclenic acid, selenium sulfide, iodochlorohydroxyquinone, bromochlorosalicyanilide, triacetin or combinations thereof.

Other antifungal agents include bensuldazic acid, benzoic acid, biphenamine, cloconazole, cloxyquin, dermostatin, halethazole, monensin, oxiconazole, nitrate, pecilocin, pyrithione, rubijervine, terbinafine, ticonazole, and undecylinic acid.

Antibacterial Agents

A variety of known antibacterial agents can be loaded into the porous wall hollow glass microspheres. A list of potential antibacterial agents can be found in "Martindale—The Complete Drug Reference", 32nd Ed., Kathleen Parfitt, (1999) on pages 112-270. Classes of useful antibacterials include aminoglycosides, antimycobacterials, cephalosporins and beta-lactams, chloramphenicols, glycopeptides, lincosamides, macrolides, penicillins, quinolones, sulphonamides and diaminopyridines, tetracyclines, and miscellaneous. In a preferred embodiment, the antibacterial agent is selected from the group consisting of metronidazole, timidazole, secnidazole, erythromycin, bactoban, mupirocin, neomycin, bacitracin, cicloprox, fluoriquinolones, ofloxacin, cephalexin, dicloxacillin, minocycline, rifampin, famciclovir, clindamycin, tetracycline and gentamycin.

Suitable aminoglycosides include antibiotics derived from *Streptomyces* and other actinomycetales, including streptomycin, framycetin, kanamycin, neomycin, paramomycin, and tobramycin, as well as gentamycin, sissomycin, netilmycin, isepamicin, and micronomycin.

Suitable antimycobacterials include rifamycin, rifaximin, rifampicin, rifabutinisoniazid, pyrazinamide, ethambutol, streptomycin, thiacetazone, aminosalicylic acid, capreomycin, cycloserine, dapsone, clofazimine, ethionamide, prothionamide, ofloxacin, and minocycline.

Cephalosporins and beta-lactams generally have activity against gram-positive bacteria and newer generations of compounds have activity against gram-negative bacteria as well. Suitable cephalosporins and beta-lactams include:

First generation; cephalothin, cephazolin, cephradine, cephaloridine, cefroxadine, cephadroxil, cefatrizine, cephalexin, pivcephalexin, cefaclor, and cefprozil.

Second generation; cephamandole, cefuroxime axetil, cefonicid, ceforanide, cefotiam, and cephamycin.

Third generation; cefotaxime, cefmenoxime, cefodizime, ceftizoxime, ceftriaxone, cefixime, cefdinir, cefetamet, cefpodoxime, ceftibuten, latamoxef, ceftazidime, cefoperazone, cefpiramide, and cefsulodin.

Fourth generation: cefepime and cefpirome

Other cephalosporins include cefoxitim, cefmetazole, cefotetan, cefbuperazone, cefminox, imipenem, meropenem, aztreonam, carumonam, and loracarbef.

Chloramphenicols inhibit gram positive and gram negative bacteria. Suitable cloramphenicols include chloramphenicol, its sodium succinate derivative, thiamphenicol, and azidamfenicol.

Suitable glycopeptides include vancomycin, teicoplanin, and ramoplanin. Suitable lincosamides include lincomycin and clindamycin, which are used to treat primarily aerobic infections.

Macrolides have a lactam ring to which sugars are attached. Suitable macrolides include erytjhromycin, as well as spiromycin, oleandomycin, josamycin, kitamycin, midecamycin, rokitamycin, azithromycin, clarithromycin, dirithromycin, roxithromycin, flurithromycin, tylosin; and streptgramins (or synergistins) including pristinamycin, and virginiamycin; and combinations thereof.

Suitable penicillins include natural penicillin and the semisynthetic penicillins F, G, X, K, and V. Newer penicillins include phenethicillin, propicillin, methicilin, cloxacillin, dicloxacillin, flucloxacillin, oxacillin, nafcillin, ampicillin, amoxicillin, bacampicillin, hetacillin, metampicillin, pivampicillin, carbenecillin, carfecillin, carindacillin, sulbenecillin, ticarcillin, azlocillin, mezlocillin, piperacillin, temocillin, mecillinam, and pivemecillinam. Lactamase inhibitors such as clavulanic acid, sulbactam, and tazobacytam are often co-administered.

Suitable quinolones include nalidixic acid, oxolinic acid, cinoxacin, acrosoxacin, pipemedic acid, and the fluoroquinolones flumequine, ciprofloxacin, enoxacin, fleroxacin, grepafloxacin, levofloxacin, lomefloxacin, nadifloxacin, norfloxacin, ofloxacin, pefloxacin, rufloxacin, sparfloxacin, trovafloxacin, danofloxacin, enrofloxacin, and marbofloxacin.

Sulphonamides and diaminopyridines include the original of the "sulfa" drugs, sulphanilamide, and a large number of derivatives, including sulfapyridine, sulfadiazine, sulfafurazole, sulfamethoxazole, sulfadimethoxine, sulfadimethoxydiazine, sulfadoxine, sulfametopyrazine, silver sulfadiazine, mafenide acetate, and sulfasalizine, as well as related compounds including trimethoprim, baquiloprim, brodimoprim, ormetoprim, tetroxoprim, and in combinations with other drugs such as co-trimoxazole.

Tetracyclines are typically broad-spectrum and include the natural products chlortetracycline, oxytetracycline, tetracycline, demeclocycline, and semisynthetic methacycline, doxycycline, and minocycline.

Suitable antibacterial agents that do not fit into one of the categories above include spectinomycin, mupirocin, newmycin, fosfomycin, fusidic acid, polymixins, colistin, bacitracin, gramicidin, tyrothricin, clioquinol, chloroquinaldol, haloquinal, nitrofurantonin, nitroimidazoles (including metronizole, timidazole and secnidazole), and hexamine.

The antibiotic and antifungal agents may be present as the free acid or free base, a pharmaceutically acceptable salt, or as a labile conjugate with an ester or other readily hydrolysable group, which are suitable for complexing with the ion-exchange resin to produce the resinate.

Local Anesthetics or Antihistamines

Local anesthetics or antihistamines may also be loaded into the hollow glass microspheres to lessen pain and itching. Suitable local anesthetics and antihistamines include benzocaine, lidocaine, dibucaine, etidocaine, benzyl alcohol, camphor, resorcinol, menthol, and diphenhdramine hydrochloride.

Anti-Inflammatory Agents

Other suitable therapeutic agents include, but are not limited to, anti-inflammatory agents. The anti-inflammatory agent can be non-steroidal, steroidal, or a combination thereof. One embodiment provides compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Dyes, Pigments, and Coloring Agents

The hollow glass microsphere can be loaded with dyes, pigments, coloring agents and combinations thereof. The dyes, pigments, or coloring agents can be protein based, chemical compounds, metals, inks, radioisotopes, fluorophores, contrast agents, and combinations thereof.

Exemplary dyes include but are not limited to Alcian yellow GXS, Alizarin, Alizarin red S, Alizarin yellow GG, Alizarin yellow R, Azophloxin, Bismarck brown R, Bismarck brown Y, Brilliant cresyl blue, Chrysoidine R, Chrysoidine Y, Congo red, Crystal violet, Fuchsin acid, Gentian violet, Janus green, Lissamine fast yellow, Martius yellow, Meldola blue, Metanil yellow, Methyl orange, Methyl red, Naphthalene black 12B, Naphthol green B, Naphthol yellow S, Orange G, Rose Bengal, Sudan II, Titan yellow, Tropaeolin O, Tropaeolin OO, Tropaeolin OOO, Victoria blue 4R, Victoria blue B, Victoria blue R, and Xylene cyanol FF.

Exemplary pigments include but are not limited to Ultramarine violet: (PV15) Silicate of sodium and aluminum containing sulfur, Han Purple: $BaCuSi_2O_6$, Cobalt Violet: (PV14) cobaltous orthophosphate, Manganese violet: $NH_4MnP_2O_7$ (PV16) Manganic ammonium pyrophosphate, Ultramarine (PB29): a complex naturally occurring pigment of sulfur-containing sodio-silicate ($Na_{8-10}Al_6Si_6O_24S_{2-4}$), Cobalt Blue (PB28) and Cerulean Blue (PB35): cobalt(II) stannate, Egyptian Blue: a synthetic pigment of calcium copper silicate ($CaCuSi_4O_{10}$), Han Blue: $BaCuSi_4O_{10}$, Prussian Blue (PB27): a synthetic pigment of ferric hexacyanoferrate ($Fe_7(CN)_{18}$), Manganese Oxide Blue: ($YIn_{1-x}Mn_xO_3$), Cadmium Green: a light green pigment consisting of a mixture of Cadmium Yellow (CdS) and Viridian ($Cr_2O_3$), Chrome green (PG17): chromic oxide ($Cr_2O_3$), Viridian (PG18): a dark green pigment of hydrated chromic oxide ($Cr_2O_3.H_2O$), Paris Green: cupric acetoarsenite, ($Cu(C_2H_3O_2)_2.3Cu(AsO_2)_2$), Scheele's Green (also called Schloss Green): cupric arsenite $CuHAsO_3$, Cadmium Yellow (PY37): cadmium sulfide (CdS), Aureolin (also called Cobalt Yellow) (PY40): Potassium cobaltinitrite ($Na_3Co(NO_2)_6$), Yellow Ochre (PY43): a naturally occurring clay of monohydrated ferric oxide ($Fe_2O_3.H_2O$), Titanium Yellow (PY53), Mosaic gold: stannic sulfide ($SnS_2$), Cadmium Red (PR108): cadmium selenide (CdSe), Sanguine, Caput Mortuum, Venetian Red, Oxide Red (PR102), Red Ochre (PR102): anhydrous $Fe_2O_3$, Burnt Sienna (PBr7), Clay earth pigments (naturally formed iron oxides), Raw Umber (PBr7): a natural clay pigment consisting of iron oxide, manganese oxide and aluminum oxide. Carbon Black (PBk7), Ivory Black (PBk9), Vine Black (PBk8), Lamp Black (PBk6), Titanium Black, Antimony White: stibous oxide ($Sb_2O_3$), Barium sulfate (PW5), Titanium White (PW6): titanic oxide ($TiO_2$), Zinc White (PW4): Zinc Oxide (ZnO), and combinations thereof.

Exemplary radioisotopes include, but are not limited to Molybdenum-99, Technetium-99m, Chromium-51, Cobalt-60, Copper-64, Ytterbium-169, Iodine-131, Iridium-192, Iron-59, Xenon-133, Xenon-127, Phosphorus-32, Potassium-42, Samarium-153 (and Strontium-89, Selenium-75, Sodium-24, Yttrium-90, Gallium-67, and combinations thereof.

Exemplary contrast agents include, but are not limited to diatrizoate, metrizoate, ioxaglate, iopamidol, iohexol, ioxilan, iopromide, iodixanol, ioversol, barium sulfate and combinations thereof.

Cells, Bacteria, and Viruses

The hollow glass microspheres can also be loaded with cells, for example bacterial or mammalian cells. The cells can be genetically engineered to express a therapeutic factor such as a protein. Alternatively, cells can be genetically engineered to secrete a therapeutic agent such as proteins, growth factors, cytokines, chemokines, and immulomodulatory agents. Exemplary cells include but are not limited to stem cells, induced pluripotent stem cells, somatic cells, umbilical cord blood cells, embryonic stem cells, cardiac cells, neural cells, muscle cells, bone cells and combinations thereof.

Vectors for expressing proteins can also be loaded into the hollow glass microspheres. These vectors include viral vectors such retroviruses, adenoviruses and naked DNA.

D. Coated Glass Microspheres

The glass microspheres can be coated. The coating can be a drug, protein, peptide, polymer, saccharide, ceramic, metal, element, chemical, nanoparticle, or a combination thereof. The coating can act to delay or prolong delivery of the contents of a hollow glass microsphere or porous wall hollow glass microsphere loaded with cargo. In some embodiments, the coating contains, or is subsequently attached to, a targeting moiety to target the glass microspheres to a specific tissue, organ or cell type. The coating can also be used to further improve the mechanical integrity, chemical durability and functionality of the microspheres.

1. Polymers

One embodiment provides glass microspheres coated with one or more polymers, surrounded by one or more polymers, or contained in one or more layers of polymer, for example encapsulated on in a liposome or micelle. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), and copolymers thereof.

The glass microsphere can be coated with one or more hydrophobic polymers. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly (orthoesters); polyanhydrides; poly(phosphazenes); poly (lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In certain embodiments, the hydrophobic polymer is an aliphatic polyester. In preferred embodiments, the hydrophobic polymer is poly(lactic acid), poly(glycolic acid), or poly(lactic acid-co-glycolic acid).

The glass microsphere be coated or in the case of hollow glass micropheres can contain one or more biodegradable polymers.

Biodegradable polymers can include polymers that are insoluble or sparingly soluble in water or other liquid media that are converted chemically or enzymatically in the body into water-soluble materials. Biodegradable polymers can include soluble polymers crosslinked by hydolyzable crosslinking groups to render the crosslinked polymer insoluble or sparingly soluble in water.

Exemplary biodegradable polymers coating the glass microspheres include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof.

The glass microspheres can be coated with or surrounded by one or more amphiphilic polymers. Amphiphilic polymers can be polymers containing a hydrophobic polymer block and a hydrophilic polymer block. The hydrophobic polymer block can contain one or more of the hydrophobic polymers above or a derivative or copolymer thereof. The hydrophilic polymer block can contain one or more of the hydrophilic polymers above or a derivative or copolymer thereof. In preferred embodiments the amphiphilic polymer is a di-block polymer containing a hydrophobic end formed from a hydrophobic polymer and a hydrophilic end formed of a hydrophilic polymer. In some embodiments, a moiety can be attached to the hydrophobic end, to the hydrophilic end, or both.

In preferred embodiments the glass microspheres are coated with or surrounded by a first amphiphilic polymer having a hydrophobic polymer block, a hydrophilic polymer block, and targeting moiety conjugated to the hydrophilic polymer block; and a second amphiphilic polymer having a hydrophobic polymer block and a hydrophilic polymer block but without the targeting moiety. The hydrophobic polymer block of the first amphiphilic polymer and the hydrophobic polymer block of the second amphiphilic polymer may be the same or different. Likewise, the hydrophilic polymer block of the first amphiphilic polymer and the hydrophilic polymer block of the second amphiphilic polymer may be the same or different.

In particularly preferred embodiments the glass microspheres are coated with biodegradable polyesters or polyanhydrides such as poly(lactic acid), poly(glycolic acid), and poly(lactic-co-glycolic acid). The glass microspheres can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly (caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker.

The glass microspheres can also be coated with or surrounded by one or more polymer conjugates containing end-to-end linkages between the polymer and a targeting moiety or a detectable label. For example, a modified polymer can be a PLGA-PEG-peptide block polymer.

The glass microspheres can be coated with or surrounded by a mixture or blend of two or more polymers. The glass microspheres may contain a first polymer having a targeting moiety and a second polymer not having the targeting moiety. By adjusting the ratio of the targeted and non-targeted polymers, the density of the targeting moiety on the exterior of the particle can be adjusted. In some embodiments the ratio is optimized to enhance the targeting and/or adhesion of the glass particles to a desired tissue such as bone.

The glass microspheres can contain be surrounded by or contained in an amphiphilic polymer having a hydrophobic end, a hydrophilic end, and a targeting moiety attached to the hydrophilic end. In some embodiments the amphiphilic macromolecule is a block copolymer having a hydrophobic polymer block, a hydrophilic polymer block covalently coupled to the hydrophobic polymer block, and a targeting moiety covalently coupled to the hydrophilic polymer block. For example, the amphiphilic polymer can have a conjugate having the structure A-B-X where A is a hydrophobic molecule or hydrophobic polymer, preferably a hydrophobic polymer, B is a hydrophilic molecule or hydrophilic polymer, preferably a hydrophilic polymer, and X is a targeting moiety. Preferred amphiphilic polymers include those where A is a hydrophobic biodegradable polymer, B is PEG, and X is a targeting moiety that targets, binds, and/or adheres to bone or other desired tissue.

The glass microsphere can be surrounded by, or contained within, polymerized fibrin. Fibrin is the end-product of the biological clotting cascade, whereby soluble fibrinogen is converted to fibrin by thrombin. Fibrinogen is a glycoprotein produced in vertebrate organisms (including humans) and circulates in the blood plasma. Fibrinogen exists in-vivo as a hexamer of two sets of 3 different subunits. Upon cleavage of fibrinogen by thrombin (to form fibrin), the fibrin polymerizes end to end to form insoluble fibers that subsequently are crosslinked and form a biogel. Fibrin as a coating agent is a biologically active coating agent that is usually derived by purification from human plasma and thus contains attached growth factors and cytokines such as are usually present in human plasma. These cytokines and growth factors are well known to those skilled in these arts. See Mann K G, Lundblad R L, Fenton J. Chemistry and Biology of Thrombin. Ann Arbor Science Publishers, and Mosesson M W. Fibrinogen and fibrin structure and functions. J Thromb Haemost 2005; 3: 1894-904, both incorporated herein by reference.

In a preferred embodiment, the glass microspheres are coated in and contained within a hydrogel consisting of polymerized fibrin treated by vortex mixing to shear the fibers and reduce viscosity. In another preferred embodiment, the glass microspheres are coated in a thin (less than 1000 nm) polymerized fibrin shell that is subsequently reacted with factor XIII to crosslink the fibrin fibers.

In some embodiments the glass microsphere is surrounded by or contained in a first amphiphilic polymer having the structure A-B-X as described above and a second amphiphilic polymer having the structure A-B, where A and B in the second amphiphilic macromolecule are chosen independently from the A and B in the first amphiphilic macromolecule, although they may be the same.

One embodiment provides glass microspheres coated with a coating agent to maximize half-life and targeting of the glass microspheres to a desired tissue or organ.

2. Targeting Moieties

The glass microspheres can be targeted to a specific tissue or organ. The targeting moiety can be coated onto the glass microspheres or can be attached to a polymer that coats the glass microspheres. The targeting moiety of the glass microsphere can be an antibody or antigen-binding fragment thereof. The targeting moiety can be an RNA or protein shaped to specifically interact with the target (e.g., an RNA- or peptide-aptamer). The targeting moiety can be a small molecule or element with specific binding affinity (e.g., biotin which binds streptavidin, or iron which is bound by the transferrin receptor). The targeting moieties should have an affinity for a cell-surface receptor, cell-surface antigen, or other ligand that is specific to the target tissue.

The targeting moiety can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

Additional targets that can be recognized by the targeting moiety include VEGF/KDR, Tie2, vascular cell adhesion molecule (VCAM), endoglin and $\alpha$-5, $\beta$-3 integrin/vitronectin. The targeting peptides can be covalently associated with the polymer of the outer shell and the covalent association can be mediated by a linker.

a. Peptide Targeting Moieties

In a preferred embodiment, the targeting moiety is a peptide. Specifically, the peptide can be, but is not limited to, one or more of the following: Epidermal growth factor (EGF), hepatocyte growth factor, and $\alpha$4 integrin (which is bound by vascular cell adhesion molecule-1), or the targets of various integrins (e.g. Integrin Ligands, matrikines and matricryptins).

b. Antibody Targeting Moieties

The targeting moiety can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal.

The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, F(ab')2, dsFv, sFv, diabodies, and triabodies. In certain embodiments, the antibody is a single chain antibody.

c. Aptamer Targeting Moieties

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

d. Additional Moieties

The glass microspheres can contain one or more polymer conjugates containing end-to-end linkages between the polymer and a moiety. The moiety can be a targeting moiety, a detectable label, or a therapeutic, prophylactic, or diagnostic agent. For example, a polymer conjugate can be a PLGA-PEG-phosphonate. The additional targeting elements may refer to elements that bind to or otherwise localize the glass microspheres to a specific locale. The locale may be a tissue, a particular cell type, or a subcellular compartment. The targeting element of the glass microsphere can be an antibody or antigen binding fragment thereof, an aptamer, or a small molecule (less than 500 Daltons).

The glass microspheres can also contain a detectable label, such as, a radioisotope, a fluorophore (e.g., fluorescein isothiocyanate (FITC), phycoerythrin (PE)), an enzyme (e.g., alkaline phosphatase, horseradish peroxidase), element particles (e.g., gold particles) or a contrast agent. These may be encapsulated within, dispersed within, or conjugated to the polymer.

For example, a fluorescent label can be chemically conjugated to a polymer of the glass microsphere to yield a fluorescently labeled polymer. In other embodiments the label is a contrast agent. A contrast agent refers to a substance used to enhance the contrast of structures or fluids within the body in medical imaging. Contrast agents are known in the art and include, but are not limited to agents that work based on X-ray attenuation and magnetic resonance signal enhancement. Suitable contrast agents include iodine, barium and other materials.

E. Biocompatible Matrices (Gelling Agents and Hydrogels)

The glass microspheres are combined with one or more biocompatible matrices, like gelling agents and hydrogels, to produce new groups of composites. These composites have properties that can be enhanced compared to the individual components alone, as exemplified by many unique systems and composites currently in the commercial sector. There are many gelling agents. Some of the common ones are acacia, alginic acid, bentonite, Carbopols® (now known as carbomers), carboxymethylcellulose. ethylcellulose, gelatin, hydroxyethylcellulose, hydroxypropyl cellulose, magnesium aluminum silicate (Veegum®), methylcellulose, poloxamers (Pluronics®), polyvinyl alcohol, sodium alginate, tragacanth, and xanthan gum. Though each gelling agent has some unique properties, there are some generalizations that can be made.

Some gelling agents are more soluble in cold water than in hot water. Methylcellulose and poloxamers have better solubility in cold water while bentonite, gelatin, and sodium carboxymethylcellulose are more soluble in hot water. Carbomers, tragacanth, and alginic acid gels are made with tepid water.

Some gelling agents (carbomers) require a "neutralizer" or a pH adjusting chemical to create the gel after the gelling agent has been wetted in the dispersing medium.

1. Carbomer

Carbomer is a generic name for a family of polymers known as Carbopol®. Carbopols® were first used in the mid 1950s. As a group, they are dry powders with high bulk densities, and form acidic aqueous solutions (pH around 3.0). They thicken at higher pHs (around 5 or 6). They will also swell in aqueous solution of that pH as much as 1000 times their original volume. Their solutions range in viscosity from 0 to 80,000 centipoise (cps). Some examples of this group of gelling agents are:

Carbopol® 910 has viscosity of 3,000-7,000 cps and is effective in low concentrations and provides a low viscosity formulation;

Carbopol® 934 has a viscosity of 30,500-39,400 cps and is effective in thick formulations such as emulsions, suspensions, sustained-release formulations, transdermals, and topicals;

Carbopol® 934P has a viscosity of 29,400-39,400 cps with the same properties as 934, but is intended for pharmaceutical formulations;

Carbopol® 940 has a viscosity of 40,000-60,000 cps and is effective in thick formulations, has very good clarity in water or hydroalcoholic topical gels; and Carbopol® 941 has a viscosity of 4,000-11,000 cps and produces low viscosity gels with very good clarity.

Carbomer polymers are best introduced into water by slowly sprinkling a sieved powder into the vortex created by rapid stirring. This should prevent clumping. Once all of the powder has been added, the stirring speed should be reduced to decrease the possibility of entrapping air bubbles in the formulation.

As mentioned, when the carbomer is dispersed, the solution will have a low pH. A "neutralizer" is added to increase the pH and cause the dispersion to thicken and gel. Some neutralizing agents are sodium hydroxide, potassium hydroxide, and triethanolamine. If the inorganic bases are used to neutralize the solution, a stable water soluble gel is formed. If triethanolamine is used, the gel can tolerate high alcohol concentrations. The viscosity of the gel can be further manipulated by propylene glycol and glycerin (to increase viscosity) or by adding electrolytes (to decrease viscosity).

2. Cellulose Derivatives

The cellulose derivatives (methylcellulose, hydroxyethylcellulose, hydroxypropylcellulose, hydroxypropylmethylcellulose, and carboxymethylcellulose) are commonly used. There are some commonalties in these compounds, and each one has their unique properties.

Methylcellulose has a viscosity of 1500 cps and makes thinner gels with high tolerance for added drugs and salts. It is compatible with water, alcohol (70%), and propylene glycol (50%) and hydrates and swells in hot water. The powder is dispersed with high shear in about ⅓ of the required amount of water at 80° C. to 90° C. Once it is dispersed, the rest of the water (as cold water or ice water) is added with moderate stirring. Maximum clarity, hydration, and viscosity will be obtained if the gel is cooled to 0-10° C. for about a hour.

Hydroxyethylcellulose makes thinner gels that are compatible with water and alcohol (30%). It hydrates and swells in cool water (about 8-12 hours). It forms an occlusive dressing when lightly applied to the skin and allowed to dry Hydroxypropylcellulose makes thinner gels with high tolerance for added drugs and salts and is compatible with alcohols and glycols. It hydrates and swells in water or hydroalcoholic solution. The powder is sprinkled in portions into water or hydroalcoholic solution without stirring and allowed to thoroughly wet. After all of the powder is added and hydrated (about 8-12 hours), the formulation can be stirred or shaken. It is a good gelling agent if 15% or more of an organic solvent is needed to dissolve the active drug.

Hydroxypropylmethylcellulose makes thicker gels but has a lower tolerance for positively charged ions. It is compatible with water, alcohol (80%) and disperses in cool water. It is a good gelling agent for time released formulations.

Carboxymethylcellulose is generally used as the sodium salt. It makes thicker gels but has less tolerance than hydroxypropylmethylcellulose. It has a maximum stability at pH 7-9 and is compatible with water and alcohol. It disperses in cold water to hydrate and swells. It is then heated to about 60° C. Maximum gelling occurs in 1-2 hours.

Poloxamer (Pluronics®) are copolymers of polyoxyethylene and polyoxypropylene. They will form thermoreversible gels in concentration ranging from 15% to 50%. This means they are liquids at cool (refrigerator) temperature, but are gels at room or body temperature. Poloxamer copolymers are white, waxy granules that form clear liquids when dispersed in cold water or cooled to 0-10° C. overnight.

Pluronic® F-127 is often combined with a lecithin and isopropyl palmitate solution to make what is called a "PLO gel." This is a slight misnomer, since the final product is actually an emulsion. The confusion comes from using a gel as one of the ingredients for the emulsion. A syringe adaptor "PLO gel" is made by combining a Pluronic® F-127 gel and a lecithin/isopropyl palmitate syrup. The two components are made and stored separately. When it is time to compound a formulation, water soluble drugs are dissolved in the Pluronic® gel or oil soluble drugs are dissolved in the lecithin syrup. If a small quantity of formulation is to be made, each of the components can be put into a syringe and the two syringes are connected by a adapter. The mixture is forced between the two syringes and the shear caused by the passing the mixture through the adapter will create the "PLO gel."

3. Ionic Hydrogels

Ionic polysaccharides, such as alginates or chitosan, can be used to suspend the disclosed glass microspheres. In one embodiment, the hydrogel is produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

Glass microspheres are mixed with an alginate solution, the solution is delivered to a desired site in a subject and then solidifies in a short time due to the presence in vivo of physiological concentrations of calcium ions. Alternatively, the solution is delivered to the support structure prior to implantation and solidified in an external solution containing calcium ions. In addition, the support structure itself can be coated with or contain the appropriate ions, for example, calcium cations, to cause an ionic hydrogel to solidify once introduced into the support structure.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorus atoms separated by alternating single and double bonds. Each phosphorus atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Polyphosphazenes that erode in vivo have at least two different types of side chains: acidic side groups capable of forming salt bridges with multivalent cations, and side groups that hydrolyze under in vivo conditions, e.g., imidazole groups, amino acid esters, glycerol, and glucosyl. Degradable polymers, i.e., polymers that dissolve or degrade within a period that is acceptable in the desired application (usually in vivo therapy), will degrade in less than about five years and most preferably in less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described herein are known to those of ordinary skill in the art. See, for example Concise Encyclopedia of Polymer Science and Engineering, J. I. Kroschwitz, editor (John Wiley and Sons, New York, N.Y., 1990). Many polymers, such as poly(acrylic acid), alginates, and PLURONICS™, are commercially available. Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

4. Temperature-Dependent Hydrogels

Temperature-dependent, or thermosensitive, hydrogels can be use with the disclosed glass microspheres. These hydrogels have so-called "reverse gelation" properties, i.e., they are liquids at or below room temperature, and gel when warmed to higher temperatures, e.g., body temperature. Thus, these hydrogels can be easily applied at or below room temperature as a liquid and automatically form a semi-solid gel when warmed to body temperature. Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers.

These copolymers can be manipulated by standard techniques to alter physical properties such as their porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration. These gels have diffusion characteristics capable of allowing cells to survive and be nourished.

U.S. Pat. No. 4,188,373 describes the use of PLURONIC™ polyols in aqueous compositions to provide thermal gelling aqueous systems. U.S. Pat. Nos. 4,474,751, ’752, ’753, and 4,478,822 describe drug delivery systems that utilize thermosetting polyoxyalkylene gels. With these systems, both the gel transition temperature and/or the rigidity of the gel can be modified by adjusting the pH and/or the ionic strength, as well as by the concentration of the polymer.

5. pH-Dependent Hydrogels

Other hydrogels suitable for use with the disclosed glass microspheres are pH-dependent. These hydrogels are liquids at, below, or above specific pH values, and gel when exposed to specific pH values, e.g., 7.35 to 7.45, which is the normal pH range of extracellular fluids within the human body. Thus, these hydrogels can be easily administered as a liquid and automatically form a semisolid gel when exposed to body pH. Examples of such pH-dependent hydrogels are TETRONICS™ (BASF-Wyandotte) polyoxyethylene-polyoxypropylene polymers of ethylene diamine, poly(diethyl aminoethyl methacrylate-g-ethylene glycol), and poly(2-hydroxymethyl methacrylate). These copolymers can be manipulated by standard techniques to affect their physical properties.

6. Light Solidified Hydrogels

Other hydrogels that can be used in glass microspheres are solidified by either visible or ultraviolet light. These hydrogels are made of macromers including a water soluble region, a biodegradable region, and at least two polymerizable regions as described in U.S. Pat. No. 5,410,016. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light.

Examples of such light solidified hydrogels include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity. Light solidified hydrogels are useful, for example, for direct painting of the hydrogel-cell mixture onto damaged tissue.

Regardless of type, a hydrogel used with the glass microspheres should be biocompatible, and, preferably, able to solidify rapidly in vivo (i.e., in about 5 minutes or so following delivery to the support structure).

III. Formulations

The glass microsphere composites can be formulated to contain an effective amount of glass microspheres in a biocompatible matrix appropriate for administration to an individual in need thereof as a bulking agent, cosmetic agent, colorant, or to treat a pathology, disease or syndrome.

The composite can be formulated for parenteral delivery, such as injection or infusion by altering the composite formulation. The viscosity of this system can then be tailored to the applications desired. (In FIGS. 2A, 2B and 2C, the viscosities of solid and hollow glass microspheres are shown as a function of several different matrix loading ratios) The formulation can be administered directly by injection.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The matrix can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the nanoparticles can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or nanoparticles.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

A sterile injectable material can be prepared by incorporating the glass microsphere and matrix composite in the required amount in the appropriate solvent or dispersion medium with one or more of the excipients listed above, as required. The injectable material can be sterilized either before or after compounding. Generally, dispersions are prepared by incorporating the desired sterilized glass microspheres into a sterile matrix which can also contain the dispersion medium and required other ingredients from those listed above. In the case of sterile powders for the preparation of sterile injectable solutions, the preferred methods of preparation are vacuum-drying and freeze-drying techniques which yield a powder of the glass microsphere and matrix composite plus any additional desired ingredient from a previously sterile-filtered solution thereof.

The composite may also contain one or more tonicity agents to adjust the isotonic range of the formulation. Suitable tonicity agents are well known in the art. Examples include glycerin, mannitol, sorbitol, sodium chloride, and other electrolytes.

The composite may also contain one or more preservatives to prevent bacterial contamination of the preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

The composite may also contain one or more excipients known art, such as dispersing agents, wetting agents, and suspending agents.

A preferred embodiment provides the composite of glass microspheres in a gel matrix as described above. For example, in one embodiment the composite consists of combining glass microspheres with the gel matrix "PLO gel", made by combining a Pluronic® F-127 gel and a lecithin/isopropyl palmitate syrup. The two components are made and stored separately. When it is time to compound a formulation, water soluble drugs are dissolved in the Pluronic® gel or oil soluble drugs are dissolved in the lecithin syrup. If a small quantity of formulation is to be made, each of the components can be put into a syringe and the two syringes are connected by an adapter. The mixture is forced between the two syringes and the shear caused by the passing the mixture through the adapter will create the final composite material. In one embodiment, the force required to eject the composite is less than 10 N, preferably between 2 and 8 N inclusive.

IV. Methods of Use of Implants with Glass Microsphere Composites

A. Soft Tissue Augmentation

Hoarseness will affect nearly ⅓ of the population at some point in their life. For patients whose voice is related to their ability to work (e.g. singers, teachers, managers, etc.) this can represent a threat to their income potential. Occasionally surgical intervention is required. The most common treatment is to physically augment the vocal fold(s), making it easier to bring them together and achieve vibration and voice. This is most often done by injection of soft tissue filler through a needle. Existing injectable filler materials are inadequate, especially if a long-lasting filler is desired. Numerous short-lived fillers are available, with resorption (and need for repeat surgery) over weeks to months. Essentially only a single viable product exists for longer lasting tissue augmentation, namely calcium hydroxyapatite particles. These are resorbed at a variable rate from 12 months to several years, but are not permanent. At the microscopic level, these calcium hydroxyapatite particles are not spherical, and have a rough surface. Injectable products containing these types of calcium hydroxyapatite particles have high viscosity and are difficult to inject. One embodiment provides a method for treating hoarseness in subject in need thereof by administering an effective amount of the disclosed glass microsphere composites.

The disclosed glass microsphere composites have significant advantages over calcium hydroxyapatite and other particles because the silica-based glass microsphere compositions can be more durable and nearly permanent. This results in a reduced likelihood of need for repeat surgery. Another advantage of the disclosed composite is the smooth outer surface, resulting in a low inflammatory response in the subject. Additionally, the composites including gel compositions have a significant ease-of-use advantage requiring lower force for injection due in part to the morphology and smooth surfaces of the microspheres. A comparison of force required to eject calcium hydroxyapatite implant compared to a microsphere and gel composite is presented in FIG. 4.

One embodiment provides a method for soft tissue augmentation in a subject in need thereof, by administering a glass microsphere composite to soft tissue of the subject in need of augmentation. The glass microsphere composites include solid glass microspheres, hollow glass microspheres, porous wall hollow glass microspheres or combinations thereof in tailored size distributions and mixtures, and matrix ratios, which induce little or no inflammatory reaction in the subject. In one embodiment, the silica-based glass microsphere composition has limited bioabsorability or biodegradability. Thus, the glass microsphere composites provide a more permanent tissue augmentation. The hollow glass microspheres can also be loaded with cargo as described above. In one embodiment the soft tissue to be treated consists of the tissue lateral to the vocal cords; augmentation using various compounds to this area is commonly performed by those skilled in the art to improve phonation, or to reduce aspiration from incomplete glottic closure. In another embodiment, the soft tissue to be treated consists of the vocal cords themselves, more properly termed the vocal folds. In a more preferred embodiment, the soft tissue consists of the superficial layer of the lamina propria of the vocal fold. This is the region of the vocal fold responsible for the majority of the vibratory function of the vocal folds. It can be damaged in the case of vocal fold scar, and result in permanent hoarseness due to impaired vibration. Currently, no technique or implant material is known to those skilled in the art, which approaches the vibratory and mass/density properties of this superficial layer of the lamina propria. Existing implants and materials have, for the most part, high density and undesirable vibratory properties. As an analogy, a small weight placed on a guitar or piano string will significantly alter the resulting vibratory characteristics and sound. Importantly, the properties of the disclosed composite can be tuned to adjust density and vibratory characteristics to match that of biologically relevant tissue. This tuning can be accomplished by selecting various combinations and proportions of types of glass microspheres and size distributions, as well as coatings or cargoes of varying density, and matrix composition. In a most preferred embodiment, the soft tissue consisting of the superficial layer of the lamina propria is implanted with the glass microsphere composite, optimized to provide advantageous mass density and vibratory characteristics to treat vocal fold scar or other medical conditions.

The glass microsphere compositions are suitable for administration within fascial or other biologic compartments, or in submucosal, subcutaneous, intradermal, hypodermal, intramuscular, subperiosteal, or subperichondrial tissue. In one embodiment, the biologic compartment includes a joint space affected by degenerative or traumatic changes resulting in loss or damage to articular cartilage. In a preferred embodiment the composite is optimized to provide a low-friction, highly durable joint articular surface. In a more preferred embodiment, the composite includes glass microspheres with size ranging from about 5 microns to about 60 microns, more preferably 10 to 40 microns. In an even more preferred embodiment, the glass microspheres can be coated to enhance mechanical and chemical properties.

In one embodiment, the composite is suitable for administration to tissues covered by skin or mucosa that is exposed in public, such as facial tissue. In a preferred embodiment, the glass microsphere composites are administered to deep subcutaneous or to submuscular/supraperiostal tissue, optionally in more than one layer. Deep subcutaneous or submuscular/supraperiostal administration further prevents or diminishes migration of the particles away from the desired site. According to this embodiment, a major volume of composite, or more than 50% (v/v), preferably more than 60% (v/v), more preferably more than 70% (v/v), of the composite consists of glass microspheres within the desired size and type distributions under physiological conditions.

In another preferred embodiment, the glass microsphere composites further include other suitable additives, such as local anesthetics, anti-inflammatory drugs, antibiotics and other suitable supportive medications, e.g. bone growth factors or cells including fibroblasts, stem cells and/or induced pluripotent stem cells or lineage reprogrammed cells.

The glass microsphere composites can be administered to a subject in need thereof for facial contouring (e.g., more pronounced cheeks or chin), for correction of concave deformities (e.g. post-traumatic, HIV associated lipoatrophy) and for correction of deep age-related facial folds. Contour deficiencies such as frown lines, worry lines, wrinkles, crow's feet, marionette lines, stretch marks, and tissue loss resulted from injury, wound, bite, surgery, or accident can be treated with the disclosed glass microsphere composites. The glass composites work particularly well with contour deficiencies of such areas as cheeks, nose, forehead and neck. The glass microspheres also work well for restoration or augmentation of breast volume, such as following mastectomy for breast cancer, or for congenitally small breasts (micromastia). Thus, the glass microsphere composites can be used for soft tissue augmentation solely for cosmetic purposes or for medical purposes, such as following trauma or degenerative disease.

The glass microsphere composites display little to no immune reaction. Some existing implant materials (e.g. Teflon®) are noteworthy for propensity towards intense fibrotic responses following implantation. While the currently popular implant materials display less intense inflammatory response than Teflon, there is still a degree of inflammation that leaves significant room for improvement. In a review article on the subject, Nicolau et al. highlighted several studies that show increased inflammatory response to particulate implants having a porous or irregular surface. Existing "microsphere" implants such as calcium hydroxyapatite actually have a very irregular surface when viewed at 400× magnification and would be more properly termed calcium hydroxyapatite particles. By comparison, the glass microspheres of the disclosed composite are smooth-surfaced and truly spherical in shape, which will aid in delivery and subsequent performance for a variety of applications.

There are instances where a short-term soft tissue augmentation is desirable, and many filler materials are adequate for this task at present. In most cases, however, a long lasting (or nearly permanent) repair option is indicated. The most commonly used long-lasting implant material currently commercially available in the United States is calcium hydroxyapatite particles delivered in a carrier gel. This product is thought to be engulfed by macrophages and degraded over months to years, and is not permanent. Glass microspheres, appropriately sized to prevent phagocytosis, should be near-permanent. Rather than months, years or even decades, there are ceramic compositions that have lasted for centuries, even in adverse environments, allowing the described glass microsphere implants to be nearly permanent and biologically inert.

All existing products have a significant portion of the injectable material being rapidly resorbed carrier, and a minority portion consisting of actual filler material. For example, commercially available calcium hydroxyapatite formulations consists of 40% CAHA and 60% methylhydroxycellulose gel. Thus, the surgeon must estimate how much resorption will take place in the days to weeks following injection, and overinject by that amount. Not only is this imprecise, but also it affords extra risk—too much augmentation of the vocal folds can lead to airway compromise. Therefore the surgeon is often forced to err on the side of injecting too little. The disclosed glass microsphere composites have low viscosity and are easy to inject even through small needle sizes. This allows far higher filler composition (theoretically up to 100% as it flows like a liquid even without matrix). This eliminates the need to overinject.

The disclosed glass microsphere compositions may be injected using a standard medical syringe and needle (21 to 27 gauge is typical) into an area of soft tissue in need of repair or augmentation. The amount of composition injected is according to the professional judgment of the medical practitioner treating the patient. In one embodiment, the force needed to injece B. Hard Tissue Augmentation The glass microsphere composites can be used for regeneration of hard tissues, such as bone, cartilage, connective tissues and the like. The composite may be formed into implants. The methods for utilizing the glass microsphere composites in the repair of bones include the repair of fractures including union and non-union fractures, bone defects, bone chips, bone erosion, bone loss, and other bone diseases or defects.

One method of hard tissue augmentation provides administering the glass microsphere composites to a hard tissue of a subject, wherein the hard tissue of the subject is in need of augmentation. In a preferred embodiment, the hard tissue is bone or cartilage. The bone can be any bone in the subject including any skeletal bone, for example facial or cranial bones as well as limb bones. In a preferred embodiment the glass microspheres are porous wall hollow glass microspheres optionally loaded with osteogenic factors, for example but not limited to: bone morphogenic proteins, TGF-beta1, stromal-derived growth factor 1 (SDF1), or non-coding RNAs to regulate osteogenic-related gene expression.

C. Delivery Systems

The hollow glass microspheres and the porous wall hollow glass microspheres can be loaded with a variety of therapeutic agents described above. The loaded glass microspheres can be administered to soft or hard tissue and thereby augment the tissue while also delivering the therapeutic agents to the tissue. The glass microsphere compositions can contain different glass microspheres loaded with different therapeutic agents. Thus a single glass microsphere composition can deliver multiple therapeutic agents. As noted above, the glass microspheres can be gated or coated to have delayed or immediate release of their cargos.

V. Kits Providing Glass Microsphere Composites

One embodiment provides a kit containing the glass microspheres, therapeutic agents for loading the glass microspheres, a biocompatible matrix such as a gelling agent, polymer, or liquid for forming a composite material containing the glass microspheres and matrix. The kit contains printed directions of use. The components can be housed in a single container. Preferably the components of the kit are sterilized. In one embodiment, the kit contains a preloaded syringe containing the glass microsphere composite.

Syringes useful for administering the glass microsphere composites include any syringe known in the art capable of delivering viscous dermal filler compositions. The syringes generally have an internal volume of about 0.4 mL to about 3 mL, more preferably between about 0.5 mL and about 1.5 mL. This internal volume is associated with an internal diameter of the syringe which affects the extrusion force needed to inject high viscosity dermal filler compositions. The internal diameters are generally about 4 mm to about 9 mm, more preferably from about 4.5 mm to about 6.5 mm. Further, the extrusion force needed to deliver the glass microsphere compositions from the syringe is dependent on the needle gauge. The gauges of needles used generally for medical purposes include gauges between about 16 G and about 31 G, more preferably about 21 G to about 27 G. A person of ordinary skill in the art can determine the correct syringe dimensions and needle gauge required to arrive at a particular extrusion force requirement.

The extrusion forces displayed by the glass microsphere composites described herein using the needle dimensions described above are applied using injection speeds that are comfortable to a patient. Comfortable to a patient is used to define a rate of injection that does not injure or cause excess pain to a patient upon injection to the soft tissue. One skilled in the art will appreciate that comfortable as used herein includes not only patient comfort, but also comfort and ability of the physician or medical technician injecting the glass microsphere composites. Although certain extrusion forces may be achievable with any injectable filler (including the glass microsphere composites), one skilled in the art understands that high extrusion forces can lead to lack of control during injection and that such lack of control may result in additional pain to the patient. The extrusion force can be fine-tuned by varying the amounts, types, and sizes of the microsphere component and/or the biocompatible matrix component of the composite, depending on the desired application. Extrusion forces of the present glass microsphere compositions can be from about 0.5 N to about 50 N, or more preferably from about 0.5 N to about 2 N, or about 1 N to about 7 N, or about 20 to about 30 N.

While several of the short-lived injectable fillers have favorable flow characteristics (e.g., are easy for the surgeon to inject), current formulations of longer-lasting implants, particularly those containing calcium hydroxyapatite, are inherently difficult to inject. The commercial formulation of calcium hydroxyapatite has lower viscosity at high temperature compared to room temperature or body temperature. Therefore in usual practice by most surgeons, the product is heated significantly above body temperature to allow smooth enough flow for injection, although the target tissue effects (at the site of implantation) of this have not been determined. The glass microsphere composites display certain nano-like alterations in physical properties, and behave much more like a liquid than a particulate material. Thus, the injection of the glass microsphere composites through a syringe is significantly easier than existing products.

The syringes and components are generally sterilized prior to use or sale. Sterilization includes any method known in the art to effectively kill or eliminate transmissible agents, preferably without substantially altering or degrading the glass microsphere compositions and any active agents.

One preferable method of sterilization of the filled syringes is by autoclave. Autoclaving can be accomplished by applying a mixture of heat, pressure and moisture to a sample in need of sterilization. Many different sterilization temperatures, pressures and cycle times can be used for this step. For example, the filled syringes may be sterilized at a temperature of at least about 120° C. to about 130° C. or greater. Moisture may or may not be utilized. The pressure applied is in some embodiments depending on the temperature used in the sterilization process. The sterilization cycle may be at least about 1 minute to about 20 minutes or more.

Sterilization also includes the use of an irradiation source which is known in the art to kill or eliminate transmissible agents. A beam of irradiation is targeted at the syringe containing the glass microsphere composite, and the wavelength of energy kills or renders the unwanted transmissible agents non-viable. Preferable energy useful include, but is not limited to ultraviolet light, gamma irradiation, visible light, microwaves, or any other wavelength or band of wavelengths which kills or eliminates the unwanted transmissible agents, preferably without substantially altering of degrading the carrier gel, gating agent, or any active agent payload. Many types of glasses have been shown to exhibit excellent radiation resistance in a variety of conditions and uses.

EXAMPLES

Example 1: Characterization of Microsphere Compositions

Preparations of a commercially available dermal filler containing calcium hydroxyappetite particles and methylhydroxycellulose gel were made by applying a small amount onto a glass slide along with a volume of aqueous mounting media and a coverslip. A similar preparation was made of one disclosed composite, namely hollow wall glass microspheres of a mixture of sizes and uncoated, combined with a methylhydroxycellulose matrix. Slides were visualized at high magnification using a combination of phase contrast and brightfield microscopy, to explore the surface properties of the two fillers.

Figures 2A, 2B:
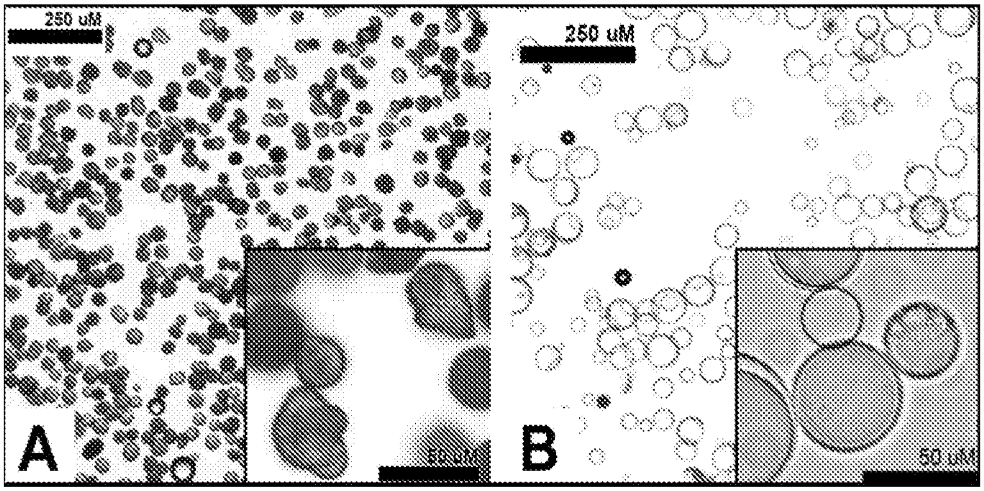
FIGS. 2A and 2B are microphotographs. Morphology differences of a commonly used dermal filler containing 40% by volume calcium hydroxyapatite particles (often inappropriately termed "microspheres") (FIG. 2A), compared to the glass microspheres of the disclosed composite (FIG. 2B).

The commercially available filler is described as containing calcium hydroxyappetite "microspheres" (quotation marks added), however as can be seen in the micrographs of FIG. 2, the particles are irregular and aspherical in shape and have a rough outer surface (FIG. 2A), compared to the smooth and spherical glass microspheres (FIG. 2B).

Next, dermal fillers were extruded several through a standard medical syringe of 1 ml volume with a standard 22-gauge needle attached. Mechanical testing was performed on a single column tabletop Instron 5844 Universal Mechanical Testing System equipped with a 2 kN load cell (Instron, Norwood Miss.) at room temperature. Merlin software (Instron, Norwood Miss., Version 5.53.00) was used to control test execution and data collection. Load (N) vs. Displacement (mm) data were obtained for each experiment and exported to Microsoft Excel (Microsoft, Redmond Wash., version 14.2.5) for further analysis. Identical syringes were prepared containing equal volumes of 4 different formulations summarized in Table 1 below:

TABLE 1

| Designation | Description |
|---|---|
| A | Commercially available calcium hydroxyapatite filler (roughly 40% particles and 60% gel) |
| B | Disclosed composite consisting of 80% by volume porous wall hollow glass microspheres of multiple sizes ranging from 20 uM to 60 uM and 20% of a 2% medium-density methylhydroxycellulose gel |
| C | Disclosed composite consisting of 40% by volume porous wall hollow glass microspheres of multiple sizes ranging from 20 uM to 60 uM and 60% of a 2% medium-density methylhydroxycellulose gel |
| D | 2% medium-density methylhydroxycellulose gel |

Figure 3:
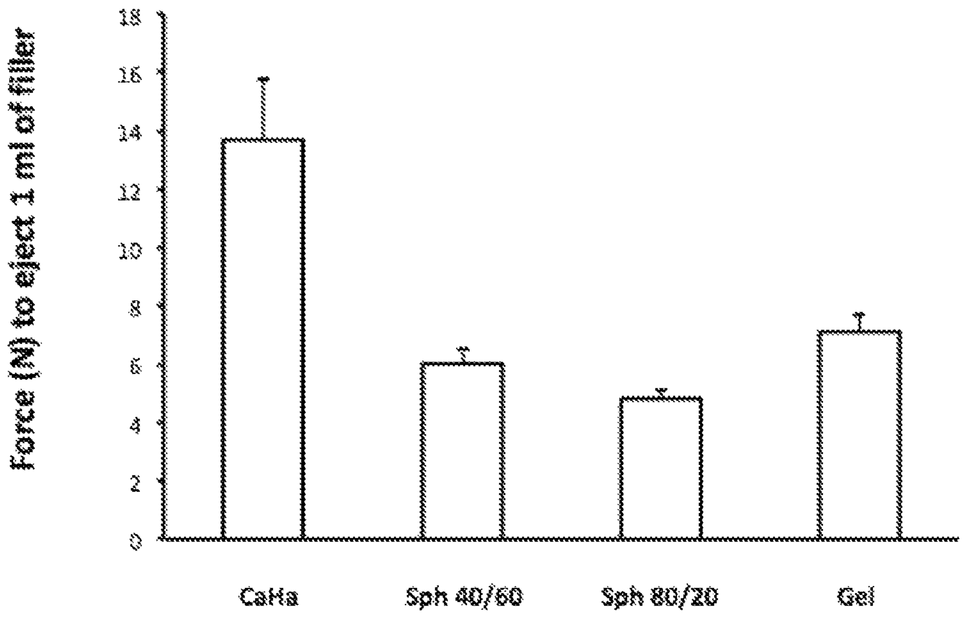
FIG. 3 is a bar graph of Force (N) to eject 1 ml of filler for calcium hydroxyapatite (CaHa), glass microsphere composition having 40% microspheres and 60% methylhydroxycellulose gel (Sph 40/60), glass microsphere composition having 80% microspheres and 20% methylhydroxycellulose gel (Sph 80/20) and methylhydroxycellulose gel alone (Gel).

As summarized in FIG. 3, the disclosed composite material displays significant reduction in force required. An interesting finding is that the formulation with higher vol % of microsphere appears to require less force; this observation is congruent with other findings when working with the microspheres that dry microspheres appear to have almost meta-properties where they flow like a liquid and not as a particulate. Certainly the smooth, spherical shape creates an advantageous situation for easy flow and lubricity (important for several of the embodiments herein disclosed).

The easier flow carries advantages not only for patient and physician comfort, but also for patient safety; by avoiding the need for high forces such as with currently available fillers, the disclosed filler allows more accurate and precise dispensing. This is especially important in microscopic surgical implantations such as into the vocal fold or surrounding tissue.

Example 2: Viscosity of Microsphere Compositions

To further explore the viscosity properties of several example formulations of the disclosed composite, composites were prepared (given in Table 2) containing solid glass microspheres, hollow glass microspheres and porous wall hollow glass microspheres combined with various aqueous and biocompatible matrices. These composites were then analyzed to determine viscosity as a function of shear rate using a Discovery Hybrid Rheometer (TA Instruments; New Castle, Del.) using multiple shear ramping from 800 to 1600 l/s, at 37 C.

TABLE 2

| Designation | Microsphere Size Range | Type of Microsphere | % Vol Microspheres | Matrix Composition |
|---|---|---|---|---|
| A | 25-35 uM | Solid | 5% | Aqueous |
| B | 25-35 uM | Solid | 10% | Aqueous |
| C | 25-35 uM | Hollow | 5% | Aqueous |
| D | 25-35 uM | Hollow | 10% | Aqueous |
| E | 25-35 uM | Hollow | 20% | Aqueous |

Figure 4A:
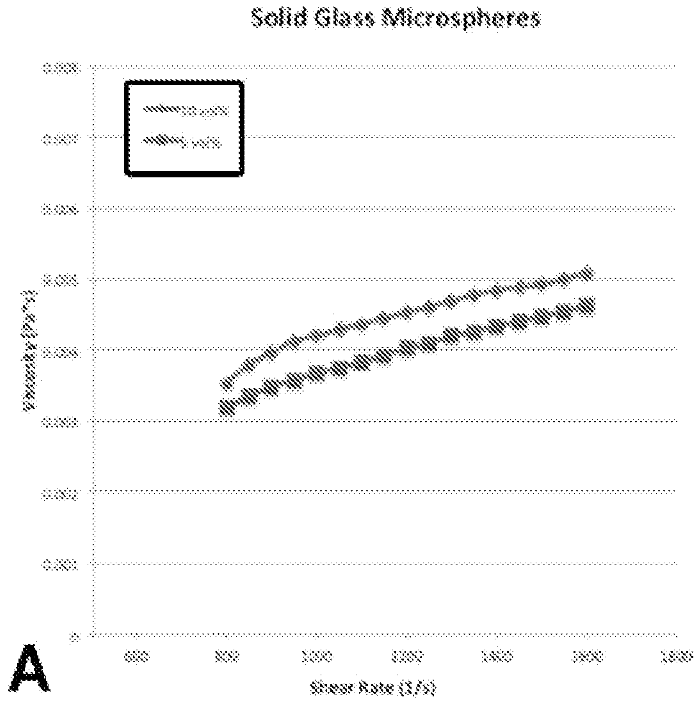
FIGS. 4A, 4B, and 4C are line graphs of viscosity measurements (Pa/s) between solid and hollow glass microspheres in a common aqueous medium is shown as a function of loading and shear rate.
Figure 4B:
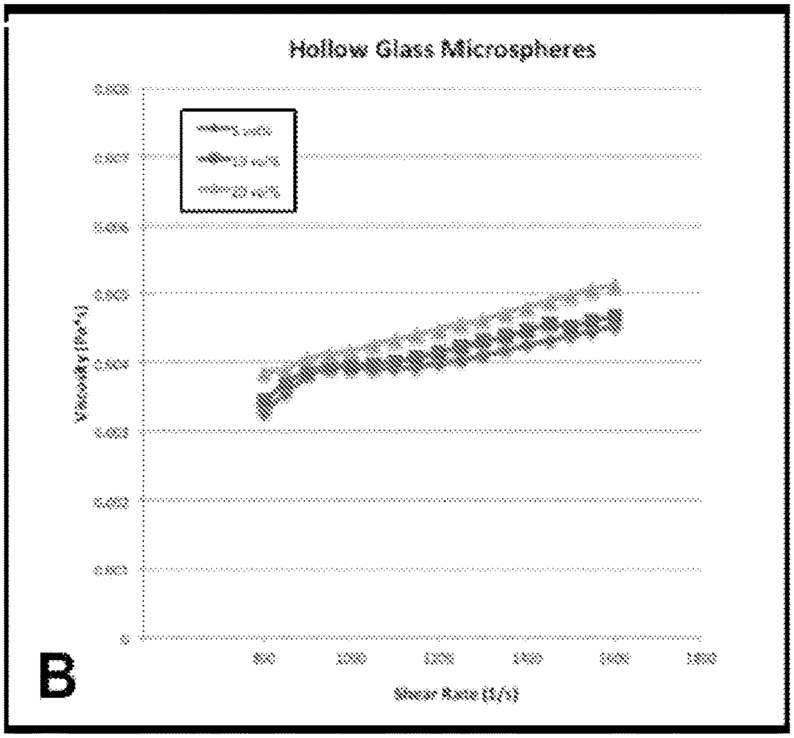
Figure 4C:
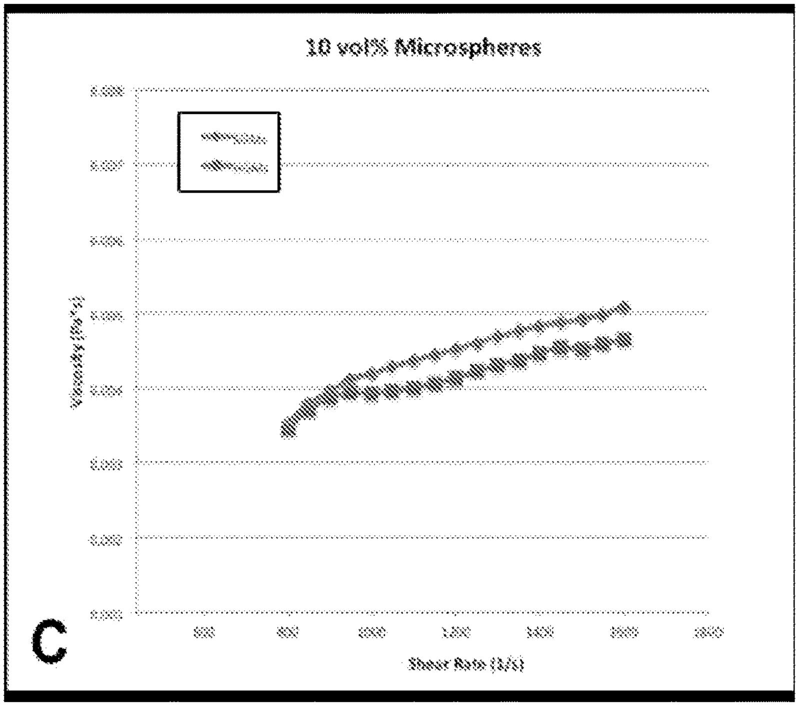

Example results are given for testing of these composites in order to measure viscosity of various combinations of microsphere types, sizes and size distributions, and ratios of the microspheres to matrix. By varying these parameters, the composite properties including 'flowability' can be fine-tuned for various applications. Shown in FIG. 4*a*, are viscosity measurements and differences of solid glass microspheres at 5 and 10 vol. % as a function of shear rate. FIG. 4B summarizes viscosity measurements for hollow glass microspheres under similar conditions. In FIG. 4*c*, solid versus hollow glass microspheres in the same matrix are compared. These data support the hypothesis that alterations in glass microsphere type and vol % within the composite affect viscosity, and that hollow glass microspheres have a lower viscosity (easier flowability) compared to solid glass microspheres. An interesting hysteresis effect is noted at lower shear rates for all microsphere types, but especially apparent for the hollow glass microspheres which may recapitulate the liquid-like flow properties observed in the dry powder form, and can be leveraged to improve the efficacy of the disclosed composite for various applications.

Example 3: Microsphere Compositions Slowly Release Cargo

Figures 5A, 5B, 5C, 5D:
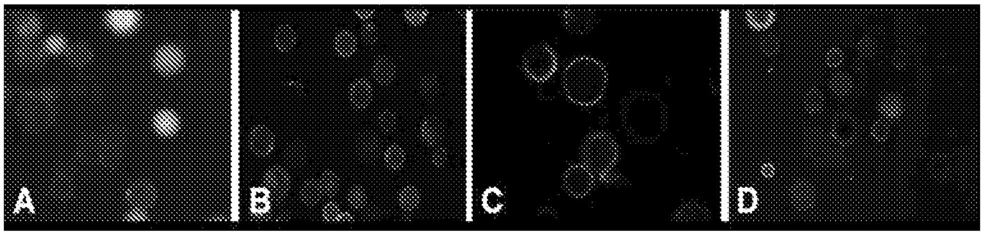
FIGS. 5A-5D are fluorescence micrograph of microspheres coated with various coatings to fine-tune properties for the intended application. Shown are fluorescence micrographs demonstrating adherence of the polymer Poly-2 Vinyl Pyridine (FIG. 5A), polyhedral oligomeric silsesquioxane (FIG. 5B), and quantum dot nano-particles (FIGS. 5C and 5D).

The glass microsphere portion of the composite can be optimized using various coatings. It was first discovered that porous wall hollow glass microspheres could be coated with the polymer Poly-2 Vinyl Pyridine (P-2VP—FIG. 5A), which has been used safely in biomedical applications. By way of further example, it was also demonstrated that the microspheres could be coated with polyhedral oligomeric silsesquioxane (POSS—FIG. 5B), and various nanomaterials, in this example quantum dot (QDot) nano-particles (FIG. 5C, FIG. 5D). The coatings (for example, Qdots, FIG. 5D) can entrap cargo within the microspheres.

Figures 6M, 6N, 6O, 6P, 6Q, 6R, 6S, 6T:
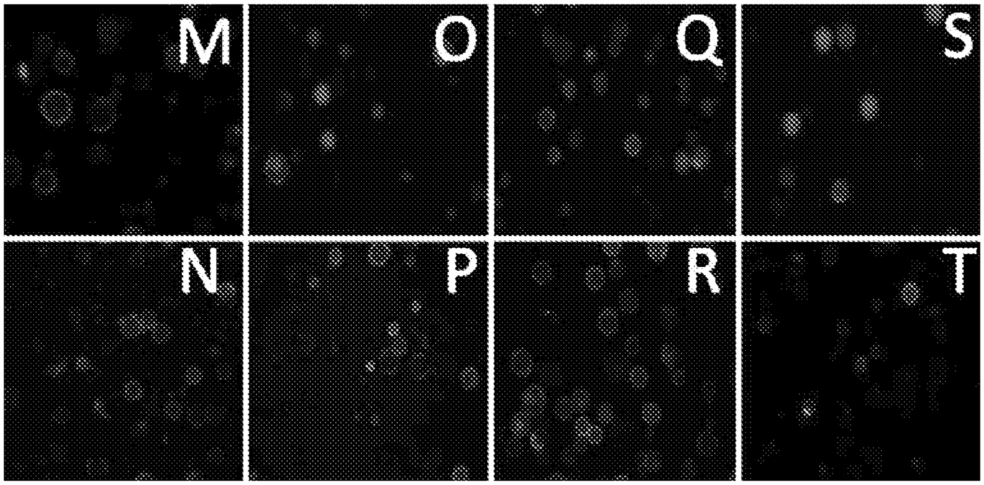
FIGS. 6M-6T are fluorescence micrographs showing that polyhedral oligomeric silsesquioxane (POSS) is helpful for coating the microspheres to affect the properties of the composite. Porous wall hollow glass microspheres were coated with varying concentrations of POSS and imaged at sequential timepoints. Uncoated (0 hrs) (FIG. 6M), Uncoated (24 hrs) (FIG. 6N), 1:2 POSS (0 hrs) (FIG. 6O), 1:2 POSS (24 hrs) (FIG. 6P), 1:4 POSS (0 hrs) (FIG. 6Q), 1:4 POSS (24 hrs) (FIG. 6R), 1:6 POSS (0 hrs) (FIG. 6S) 1:6 POSS (24 hrs) (FIG. 6T).
Figure 7A:
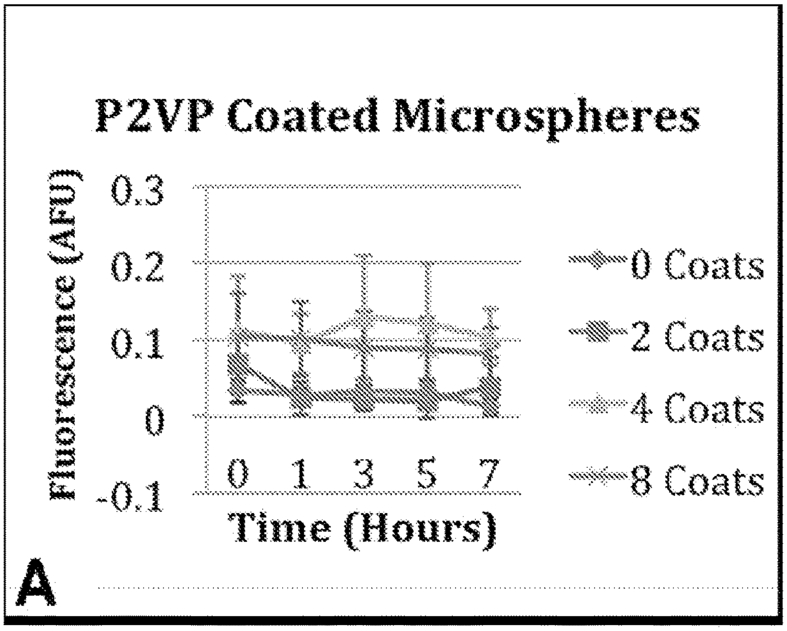
FIG. 7A is a line graph of Fluorescence (AFU) versus time (hours) for microspheres without a coating of P2VP (♦), with two coats (■), with four coats (▲), and with eight coats (×) showing that coating the microspheres can affect the release of cargo from within the microsphere portion of the composite. Microspheres coated twice with P2VP behaved similarly to the uncoated microspheres, while microspheres coated with 4 or 8 coats of P2VP showed retention of fluorescent cargo.
Figures 7B, 7C:
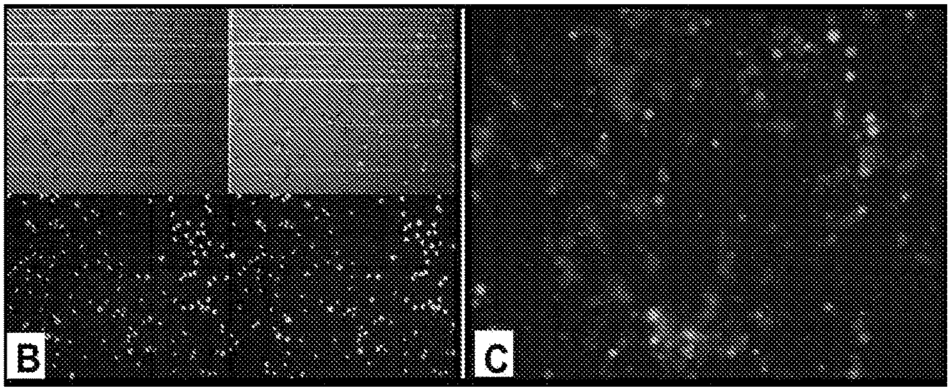
FIG. 7B is a fluorescence micrograph showing uncoated microspheres retained different amounts of cargo at day 3 post-loading. Both loaded and unloaded as well as emptied microspheres are shown by comparing the fluorescent image with the bright field image (inset).
FIG. 7C is a fluorescence micrograph of P-2VP coated microspheres at post-loading day 7 showing different degrees of cargo release. Microspheres without pores that did not load are not visible in the fluorescent image, only microspheres that once contained cargo and are nearing empty demonstrate a fluorescent ring labeling of the outer shell, examples are marked with a red line.
Figure 8:
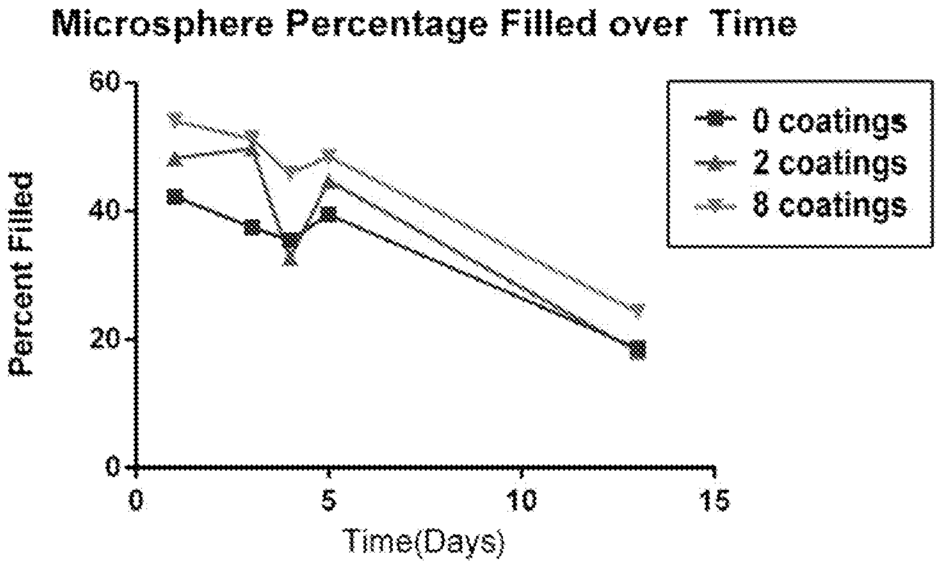
FIG. 8 is a line graph of percent filled versus time (days) for porous walled hollow glass microspheres with no P-2VP coatings (■), two coatings (▲), or eight coatings (∇). Coated microspheres were determined to hold molecules for longer than uncoated microspheres, and the number of coatings was related to retention.
Figure 9A:
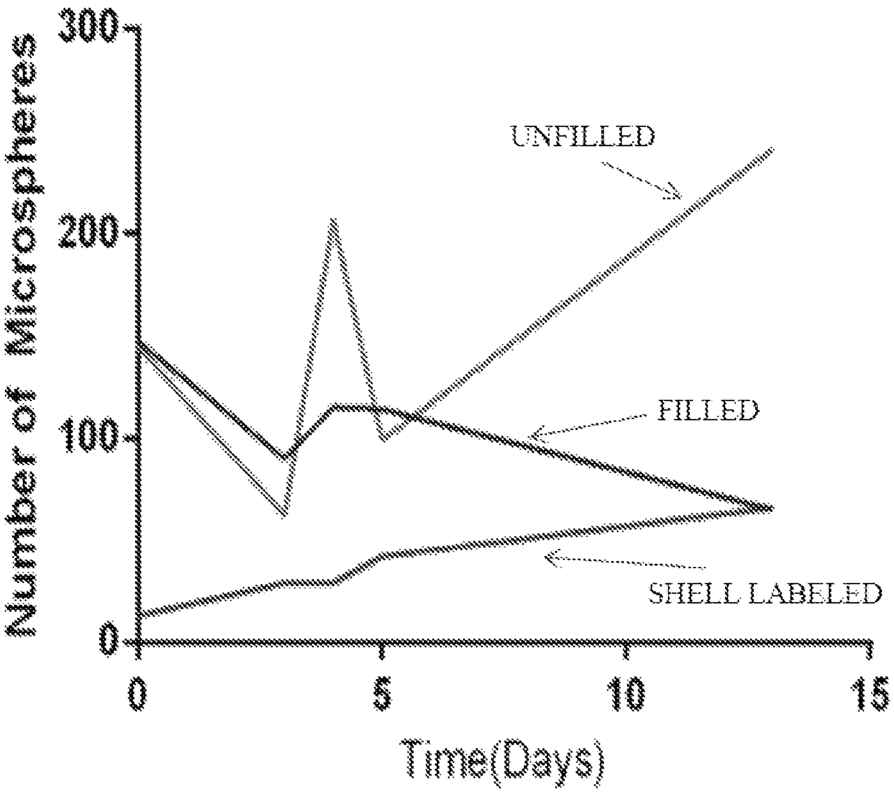
FIGS. 9A and 9B are line graphs of number of microspheres versus time (days). Change over time in the number of unfilled, partially emptied (Shell labeled) and highly filled microspheres as a function of number of P-2VP coats. The microspheres with 8 coats (FIG. 9B) showed a steady increase of cargo emptying over 13 days and a similar decline in cargo filled microspheres over that time, and it was greater than the microspheres with only 2 coats (FIG. 9B).
Figure 9B:
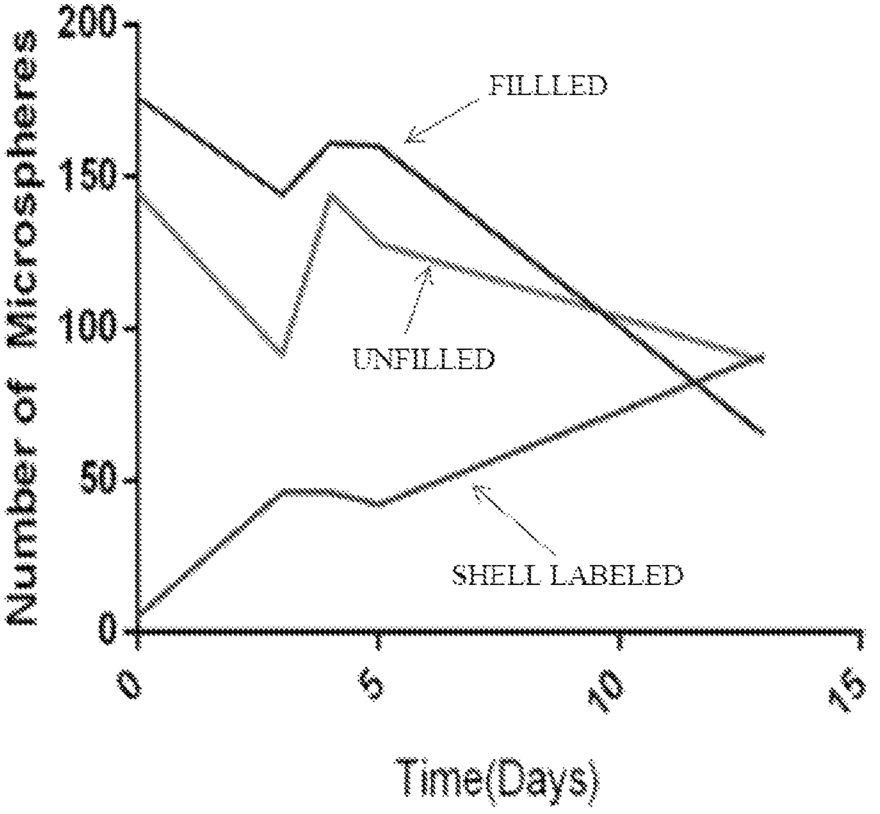
Figure 10:
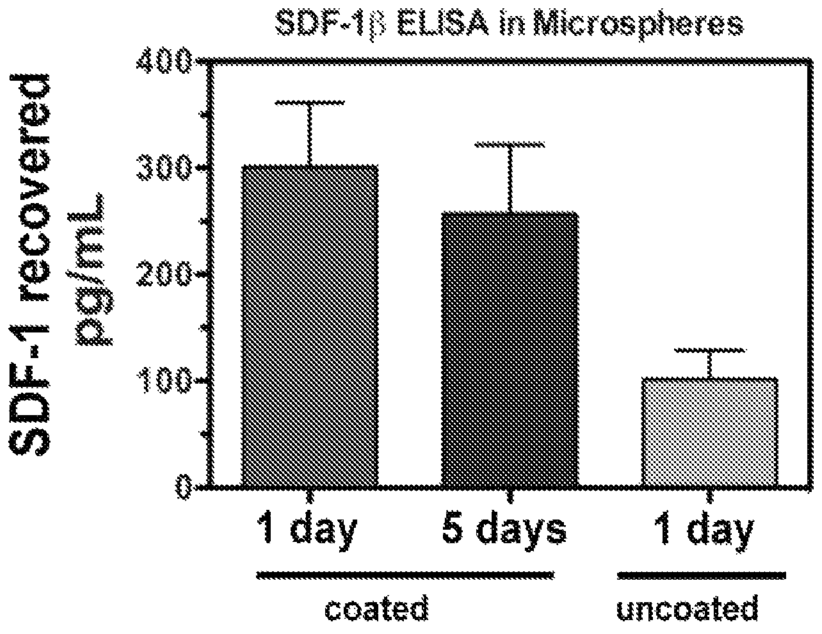
FIG. 10 is a bar graph of SDF-1 recovered (pg/ml) from coated microspheres (first and second columns from left to right, 1 day and 5 days respectively) and uncoated microspoheres (last column, 1 day) from an ELISA Assay of SDF-1 filled microspheres. It was shown that a cytokine, SDF-1, could be retained in P-2VP coated porous wall hollow glass microsphere for at least 5 days. Microspheres were loaded with SDF-1 in an aqueous media, then coated with P2VP. 1 or 5 days after the microspheres were loaded they were washed to remove any released SDF-1 then placed into fresh media into which the microspheres were crushed to release their contents so quantity of the retained SDF-1 could be assessed. The data suggests that the uncoated microspheres retained less than the coated microspheres by 24 hours and that additional, but not all, SDF-1 was released by day 5.
Figure 11:
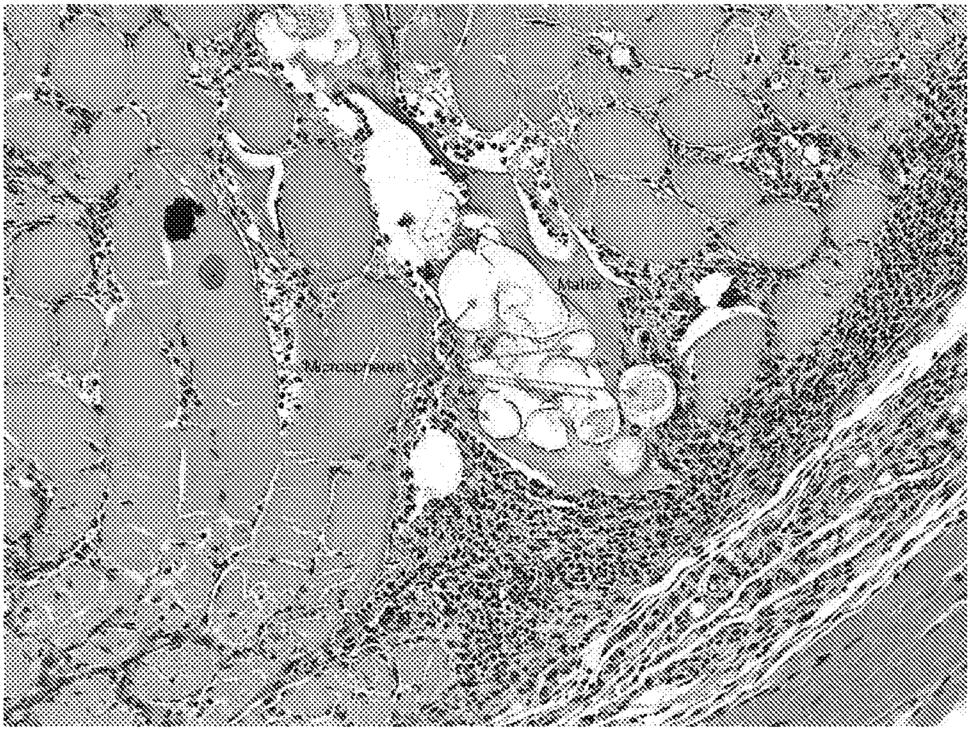
FIG. 11 is a light micrograph of one formulation of the disclosed composite, consisting of porous wall hollow glass microspheres 50% by volume combined with a biocompatible matrix (thiol-modified hyaluronic acid/collagen hydrogel), lyophilized and implanted surgically in a murine model. The micrograph image was taken at 7 days post implantation, demonstrating retention of the microsphere composite at the surgical site.

P-2VP can also entrap small molecules, compounds, and biological molecules within the microspheres. By way of example, it was demonstrated that P-2VP can entrap fluorescent molecules as well as osteogenic cytokines, like Stromal Derived Factor-1 (SDF-1), to allow delayed or extended release over time. P-2VP is an organic polymer that is known to those skilled in the art to form films on silica glass planar structures. It was demonstrated that P-2VP forms a film on spherical glass microspheres, and is efficacious to seal the microsphere pores. It was further demonstrated that increasing P-2VP coating thickness and/or concentration increases cargo retention over time (FIGS. 4-6). It was of interest to also know if the contents of a coated porous wall hollow glass microsphere would be released all at once, or gradually over time, and it appears that with coatings the release is gradual, steady and relatively linear over time (FIGS. 6 & 7). A green fluorescent fluorescein isothiocyanate (FITC) labeled molecule was used to fill the porous wall hollow glass microspheres while testing the effects of the coatings, while 8 KDa stromal cell derived factor 1 (SDF-1, also known as CXCL12) was used to fill the porous wall hollow glass microspheres for in vitro and in vivo studies (FIG. 10). The fluorescence of the actual P-2VP coating was separately measured from the fluorescence from the FITC adhering to the microspheres or the coating. Importantly the rate of porous wall hollow glass microspheres emptying over time, can be fine-tuned by changing coating amounts and formulations, depending on the application. Additionally, controlled release over time may be achieved either by use of an optimized coating or mixing porous wall hollow glass microspheres of different degrees of coating. Importantly, other methods currently known to those skilled in the art for modulating cargo release are generally limited to about hours, rather than days or longer as is the case in the disclosed composites. The latter time frame of days or longer is more translationally relevant especially in applications such as bone repair or other medical applications.

Example 4: Microspheres Compositions do not Increase Inflammation

A composite containing 50% Hollow Glass microspheres (Porous Walled) and a biocompatible matrix (HyStem-C hydrogel from ESI-BIO contains thiol-modified hyaluronan and thiol-modified denatured collagen) was prepared ahead of time as a lypholized flat circular 4 mm diameter disk. The microsphere/matrix disk was then inserted into an incision that placed the composite between muscle groups in a C57B6 mouse leg. The incision was sutured and the mouse sacrificed 1 week later for histology. FIG. 10 shows one edge of the matrix (light purple in color) containing numerous microspheres (Arrows) adjacent to muscle fibers and connective tissue. A similar inflammatory infiltrate was seen in response to hydrogel-only controls, supporting the idea that the microspheres do not result in an increased inflammatory response.

We claim:

1. An injectable composite material comprising a combination of:

(a) an effective amount of long lasting silica-based glass microspheres having a diameter of 10 μm to 100 μm; and (b) a biocompatible matrix, wherein the composite material has a viscosity tailored for a flowability sufficient to allow the composite material to flow readily through a delivery device and be implanted into soft or hard tissue in a subject, and induce little or no inflammatory response when administered to the subject, wherein the glass microsphere component comprises porous wall hollow glass microspheres, wherein the porous wall hollow glass microspheres are gated to provide controlled release of a substance loaded in the microspheres, wherein the gating agent is selected from the group consisting of dextran, colloidal starch, polymerized fibrin, and a polyvinylpyrrolidone, and wherein the porous wall hollow glass microspheres are loaded with a cargo selected from the group consisting of a therapeutic drug, biological cell, biological molecule, and colorant.

2. The composite material of claim 1, wherein the matrix component comprises a gelling agent.

3. The composite material of claim 2, wherein the gelling agent is selected from the group consisting of methylcellulose, hydroxyethylcellulose, hydroxypropylcellulose, hydroxypropylmethylcellulose, and carboxymethylcellulose.

4. A method for augmenting tissue in a subject in need thereof comprising: administering the composite of claim 1 to the subject in an amount effective to augment tissue in the subject.

5. The method of claim 4, wherein the tissue is soft or hard tissue.

6. The method of claim 4, wherein the tissue augmentation is done to treat contour deficiencies in the subject selected from the group consisting of frown lines, worry lines, wrinkles, crow's feet, marionette lines, stretch marks, and tissue volume loss resulted from injury, wound, bite, surgery, and accident.

7. The method of claim 4, wherein the tissue augmentation is done to treat vocal cord injury, defect or disease.

8. The method of claim 4, wherein the tissue augmentation is done to treat a sphincteric muscle.

9. The method of claim 8, wherein the sphincteric muscle is the urinary bladder sphincter.

10. The method of claim 8, wherein the sphincteric muscle is the upper esophageal sphincter.

11. The method of claim 4, wherein the tissue augmentation is done to treat a bone fracture, bone defect, bone loss, or bone erosion.

12. The method of claim 11, wherein the bone fracture is union or nonunion fracture.

13. A method for implanting a composite into a subject in need thereof comprising: administering the composite of claim 1 to the subject in an amount effective to provide, restore or modify the vibratory characteristics of the appropriate tissue in the subject.

14. The method of claim 13, wherein the tissue is one or both vocal folds.

15. The method of claim 14, wherein the tissue is the superficial layer of the lamina propria of one or both vocal folds.

16. A method for implanting a composite into a subject in need thereof comprising: administering the composite of claim 1 to the subject in an amount effective to provide, restore or modify joint lubricity of the appropriate a tissue in the subject.

* * * * *